(12) United States Patent
Jan et al.

(10) Patent No.: US 12,247,005 B2
(45) Date of Patent: Mar. 11, 2025

(54) PROCESS FOR CATALYTICALLY CONVERTING NAPHTHA TO LIGHT OLEFINS

(71) Applicant: UOP LLC, Des Plaines, IL (US)

(72) Inventors: Deng-Yang Jan, Elk Grove Village, IL (US); Xi Zhao, Arlington Heights, IL (US); Jaime G. Moscoso, Mount Prospect, IL (US); Mathias Paul Koljack, Glenview, IL (US); Gregory A. Funk, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 131 days.

(21) Appl. No.: 18/144,083

(22) Filed: May 5, 2023

(65) Prior Publication Data

US 2023/0357107 A1 Nov. 9, 2023

Related U.S. Application Data

(60) Provisional application No. 63/339,435, filed on May 7, 2022.

(51) Int. Cl.
C07C 5/05 (2006.01)
C07C 4/06 (2006.01)
C07C 5/32 (2006.01)

(52) U.S. Cl.
CPC ............ *C07C 5/05* (2013.01); *C07C 4/06* (2013.01); *C07C 5/322* (2013.01); *C07C 2529/40* (2013.01)

(58) Field of Classification Search
None
See application file for complete search history.

(56) References Cited

U.S. PATENT DOCUMENTS

| | | |
|---|---|---|
| 5,507,939 A | 4/1996 | Russ et al. |
| 6,080,303 A | 6/2000 | Cao et al. |
| 6,441,263 B1 | 8/2002 | O'Rear et al. |
| 10,538,711 B2 | 1/2020 | Xie et al. |
| 10,654,773 B2 | 5/2020 | Doosa et al. |
| 10,676,681 B2 | 6/2020 | Ward et al. |
| 2007/0267324 A1 | 11/2007 | Dalloro et al. |
| 2015/0209771 A1 | 7/2015 | Saka et al. |
| 2016/0237004 A1* | 8/2016 | Wang ............... B01J 29/22 |
| 2017/0369795 A1 | 12/2017 | Oprins et al. |

(Continued)

FOREIGN PATENT DOCUMENTS

| | | |
|---|---|---|
| CN | 114425376 A | 5/2022 |
| EP | 0323132 A2 | 7/1989 |
| WO | 2012071137 A1 | 10/2011 |

OTHER PUBLICATIONS

Search Report and Written Opinion for PCT/US2023/020841 dated Aug. 23, 2023.

(Continued)

*Primary Examiner* — Tam M Nguyen
(74) *Attorney, Agent, or Firm* — Paschall & Associates, LLC; James C. Paschall (57) ABSTRACT

A process for converting naphtha to light olefins comprises contacting a naphtha stream with a zeolitic catalyst to produce a light paraffin stream at conditions which dehydrogenate the naphtha to olefins, interconvert the olefins to lighter olefins and hydrogenate the lighter olefins to produce a light paraffin stream comprising ethane and propane. The catalyst may comprise a zeolite and a metal.

21 Claims, 3 Drawing Sheets

(56) References Cited

U.S. PATENT DOCUMENTS

| | | |
|---|---|---|
| 2019/0330539 A1 | 10/2019 | Al-Majnouni et al. |
| 2020/0392418 A1 | 12/2020 | Nesterenko et al. |
| 2021/0087122 A1* | 3/2021 | Sattler ...................... C07C 4/06 |
| 2021/0179514 A1 | 6/2021 | Thinon et al. |
| 2021/0363438 A1 | 11/2021 | Al-Shafei et al. |
| 2023/0399274 A1* | 12/2023 | Jan ........................ C10G 47/18 |
| 2024/0158320 A1* | 5/2024 | Nauert ..................... C07C 7/09 |

OTHER PUBLICATIONS

Search Report and Written Opinion for PCT/US2023/025187 dated Oct. 4, 2023.

Minbo Yang, "Process Modeling and Analysis of Manufacturing Pathways for Producing Ethylene and Propylene from Wet Shale Gas and Naphtha", 2017.

Search Report and Written Opinion for PCT/US2023/020995 dated Aug. 23, 2023.

\* cited by examiner

PROCESS FOR CATALYTICALLY CONVERTING NAPHTHA TO LIGHT OLEFINS

CROSS-REFERENCE TO RELATED APPLICATIONS

This application claims priority from U.S. Provisional Application No. 63/339,435, filed May 7, 2022, which is incorporated herein in its entirety.

FIELD

The field is the conversion of naphtha to light olefins. The field may particularly relate to converting naphtha to light olefins in a two-step conversion process.

BACKGROUND

Light olefin production is vital to the production of sufficient plastics to meet worldwide demand. Paraffin dehydrogenation (PDH) is a process in which light paraffins such as propane and butane can be dehydrogenated to make propylene and butylene, respectively. Dehydrogenation is an endothermic reaction which requires external heat to drive the reaction to completion.

Fluid catalytic cracking (FCC) is another endothermic process that can be tuned to produce substantial propylene. However, not every FCC unit is tuned to make substantial propylene. Also, high propylene FCC units do not make much ethylene; less than 1% of global ethylene supply comes from FCC.

The great bulk of the ethylene consumed in the production of plastics and petrochemicals such as polyethylene is produced by the thermal cracking of hydrocarbons. Steam is usually mixed with the feed stream to the cracking furnace to reduce the hydrocarbon partial pressure and enhance olefin yield and to reduce the formation and deposition of carbonaceous material in the cracking reactors. The process is therefore often referred to as steam cracking or pyrolysis. Ethane oxidative dehydrogenation is a newer catalytic process for converting ethane to ethylene which can be conducted at lower temperatures with lower carbon oxide emissions than steam cracking.

Two types of feeds are typically used for steam cracking. Ethane feed is used in regions where light hydrocarbon gases are prevalent. In regions, where gas is not abundant, naphtha feed is employed for steam cracking. Pyrolytic naphtha cracking has long set the price in the ethylene industry due to higher production cost versus pyrolytic ethane cracking. The world does not currently produce enough ethane to supply the growing demand for ethylene. Therefore, regions lacking ethane supply such as Asia and Europe rely mainly on naphtha cracking to supply ethylene. Naphtha cracking yields only about 30%-35% ethylene with the balance including both relatively high-value by-products comprising propylene, butadiene, and butene-1 and relatively low value by-products comprising pyoil, pygas, and fuel gas. Additional pressures on naphtha cracking including minimum production requirements and environmental concerns have led to the withholding of government approvals in certain regions such as China. The ethylene industry needs a more efficient, economical and environmentally friendly route to light olefins from naphtha feeds.

BRIEF SUMMARY

A process for converting naphtha to light olefins comprises contacting a naphtha stream with a catalyst to produce a light paraffin stream at conditions which dehydrogenate the paraffins to olefins, interconvert the olefins to lighter olefins and hydrogenate the lighter olefins to produce a light paraffin stream comprising ethane and propane. The catalyst may comprise a zeolite and a metal. Naphthenes may also be converted to aromatics.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

The term "Cx" is to be understood to refer to molecules having the number of carbon atoms represented by the subscript "x". Similarly, the term "Cx-" refers to molecules that contain less than or equal to x and preferably x and less carbon atoms. The term "Cx+" refers to molecules with more than or equal to x and preferably x and more carbon atoms.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

DETAILED DESCRIPTION

In the proposed process, C3-C8+ hydrocarbon feed stock is first charged to a "Naphtha to Ethane and Propane" unit to convert naphtha into desirable ethane and propane along with less desirable methane. The produced ethane is fed to an ethylene producing unit. These units provide over 75% yield of ethane to ethylene. The produced propane is fed to a propylene producing unit which provides over 85% yield of propane to propylene. The methane by-product from the naphtha conversion unit and the ethane and propane producing units can be used as a fuel including fuel needed to operate ethylene and propylene producing units which operate at elevated temperatures. Unconverted or under-converted C4+ components in the reactor outlet may be recycled to the reactor inlet for further processing to ethane and propane. Aromatics may also be recovered and further processed.

Figure 1:
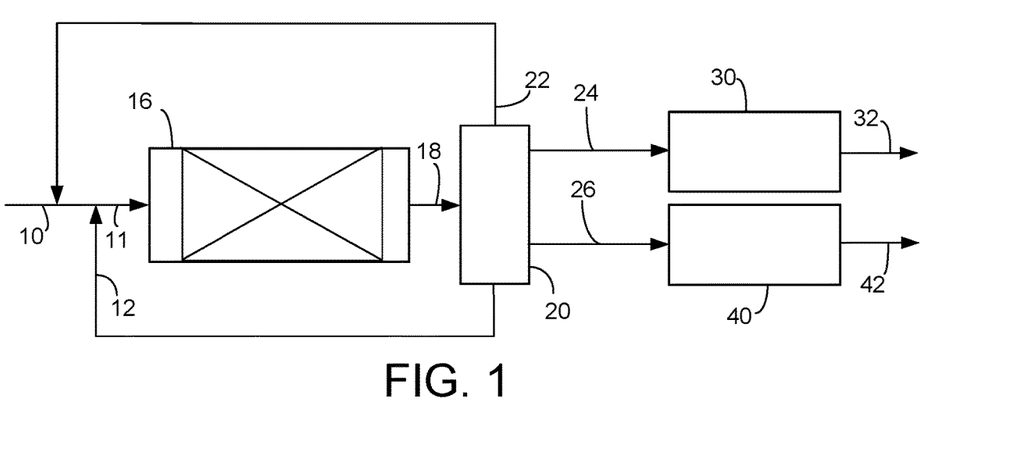
FIG. 1 is a schematic drawing of a process and apparatus of the present disclosure.

Turning to FIG. 1, a naphtha stream in line 10 may be combined with a hydrogen stream in line 22 and a heavy stream in line 12 to provide a charge stream in line 11, heated and charged to a naphtha to ethane and propane (NEP) reactor 16 to be contacted with an NEP catalyst. The naphtha stream may comprise C4 to C12 hydrocarbons preferably having a T10 between about −10° C. and about 60° C. and a T90 between about 70 and about 180° C. The naphtha feed stream may comprise normal paraffins, isoparaffins, naphthenes, and aromatics. The naphtha stream may be heated to a reaction temperature of about 300° C. to about 600° C., suitably between about 325° C. and about 550° C., and preferably between about 350° C. and about 525° C. Weight space velocity should be between about 0.3 to about 20 hr-1, suitably between about 0.5 and about 10 hr-1 and preferably between about 1 to about 4 hr-1. A total pressure should be about 0.1 to about 3 MPa (abs), preferably no more than 2 MPa (abs). At these conditions, C2-C4 yield is consistently in an excess of 80 wt %, while methane yield is less than about 10 wt %, suitably below about 8 wt % and typically below about 6 wt % and preferably no more than 5 wt %. Under these conditions, ethane can make up more than 60 wt % of the total C2 to C3 and for that matter C2 to C4 produced in the NEP reactor 16.

The hydrogen-to-hydrocarbon molar ratio is important to producing ethane and propane. The hydrogen-to-hydrocarbon ratio should be about 0.3 to about 15 and preferably about 0.5 to about 5. In a further embodiment, the hydrogen-to-hydrocarbon molar ratio may typically be no more than 5, suitably be no more than 3 and preferably be no more than 2. Low hydrogen-to-hydrocarbon ratio promotes desired reaction kinetics which are initiated with dehydrogenation. Hydrogen-to-hydrocarbon ratio may range from about 50% to about 500%, suitably no more than 300% and preferably no more than 200%, of stoichiometric requirements to convert naphtha molecules to ethane and/or propane.

The molar ratio of hydrogen to hydrocarbon depends on the feed type including paraffin, naphthene or aromatics, the feed molecular carbon number, and the desired product between predominantly ethane, predominantly propane or ethane and propane of comparable abundance as illustrated in Table 1 below. For example, converting 1 mole of propane to ethane at stoichiometry, the process would require co-feeding 0.5 moles of hydrogen. In practice, the process can operate above or below this stoichiometry of 0.5 such as 0.33 to achieve greater than 40% ethane and less than 15% methane, depending on the process design parameters such as, feed contaminants, reactor type (fixed bed, moving bed, fluidized bed), and regeneration frequency. As the carbon number of feed molecules increases from light naphtha ($C_5$-$C_7$) to full range naphtha ($C_6$-$C_{10}$) the amount of hydrogen required for the reaction increases. For example, it would require 3.5 moles hydrogen and 2.0 moles of hydrogen to fully convert 1 mole of nonane to ethane and propane, respectively. The disclosed process can operate at three to five times the hydrogen-to-hydrocarbon ratio required to stoichiometrically convert the feed molecules to ethane and propane, respectively. It can also operate at 50% of hydrogen-to-hydrocarbon ratio required to stoichiometrically convert the feed molecules to ethane and propane, respectively. The hydrogen-to-hydrocarbon ratio would also depend on the need to produce petrochemical aromatics such as benzene, toluene and xylene. Following these guidelines, one can utilize the disclosed process to convert light naphtha ($C_5$-$C_7$), full range naphtha ($C_5$-$C_{10}$) and hydrocracking-derived light and heavy naphtha comprising paraffins, naphthenic and aromatic molecules, to ethane, propane, petrochemical aromatics and mixtures thereof.

TABLE 1

| | Desired Reaction | | | |
|---|---|---|---|---|
| Carbon Number | Paraffin to Ethane | Paraffin to Propane | Naphthene to Ethane | Naphthene to Propane |
| | Stochiometric Hydrogen-to-Hydrocarbon Molar Ratio | | | |
| 3 | 0.5 | | | |
| 4 | 1 | 0.333 | | |
| 5 | 1.5 | 0.667 | 2.5 | 1.667 |
| 6 | 2 | 1.000 | 3.000 | 2.000 |
| 7 | 2.5 | 1.333 | 3.500 | 2.333 |
| 8 | 3 | 1.667 | 4.000 | 2.667 |
| 9 | 3.5 | 2.000 | 4.500 | 3.000 |
| 10 | 4 | 2.333 | 5.000 | 3.333 |

The NEP catalyst dehydrogenates the paraffin molecules in the naphtha to their olefinic analog, interconverts the olefins to lighter olefins and hydrogenates the lighter olefins to produce a light paraffin stream comprising ethane and propane. Interconversion can mean that olefins are also oligomerized to higher olefins and then these higher olefins are cracked to lower olefins. This chemical mechanism avoids or minimizes hydrogenolysis and pyrolytic cracking reactions which produce methane. Methane is an undesirable by-product that represents an opportunity lost for producing valuable ethane and propane and consumes excessive hydrogen. The NEP catalyst can also dehydrogenate naphthenes to aromatics such as benzene, toluene and xylene.

The NEP catalyst for converting naphtha to ethane and propane may contain a molecular sieve comprising large or medium pore mouths, that is, comprising 10 or 12 member rings, respectively. Examples of suitable molecular sieves include MFI, MEL, MFI/MEL intergrowth, MTW, TUN, UZM-39, IMF, UZM-44, UZM-54, MWW, UZM-37, UZM-8, UZM-8HS. Examples of suitable molecular sieves further include FER, AHT, AEL (SAPO-11), AFO (SAPO-41), MRE, MFS, EUO-1, TON (ZSM-22), MTT (ZSM-23) and UZM-53. Additional molecular sieves with larger pores include FAU, EMT, FAU/EMT intergrowth, UZM-14, MOR, BEA, UZM-50, MTW, ZSM-12. Additional examples include MSE and UZM-35.

MFI is a suitable NEP catalyst. It will be appreciated that ZSM-5 is an MFI-type aluminosilicate zeolite belonging to the pentasil family of zeolites and having a chemical formula of $Na_nAl_nSi_{96-n}O_{192} \cdot 16H_2O$ (0<n<10). In various embodiments, the ZSM-5 zeolite may comprise a silica-to-alumina molar ratio of 20 to 1000, 20 to 800, 20 to 600, 25 to 400, 25 to 200 or 25 to 80. In various embodiments, the ZSM-5 zeolite may comprise a crystal size in the range of 10 to 600 nm, 20 to 500 nm, 30 to 450, 40 to 400 nm, or 50 to 300 nm.

The NEP catalyst may comprise a bound zeolite. The binder may comprise an oxide of aluminum, silicone, zinc, titanium, zirconium and mixtures of thereof. In an embodiment, the binder may comprise a phosphate in the binder or a phosphate of the forenamed oxide binder materials. Preferably, the binder is an aluminum phosphate. The MFI zeolite may be supported in an alumina containing binder such as aluminum phosphate.

MFI zeolite slurry may be first mixed with a binder in the form of colloidal suspension (sol) and gelling reagent and then dropped into hot oil to make spheres controlled to produce ⅟₆₄-inch to about ⅟₁₀-inch diameter calcined supports. Spheres may be washed with ammonia to remove sodium ions from the zeolite, dried and calcined to remove the organic structural directing agent (OSDA) from the synthesized zeolite. Optionally, the calcined support may be ammonium-ion exchanged using an ammonium nitrate solution to remove residual sodium ions and dried at about 110° C.

In an embodiment, the NEP catalyst comprises a metal on the catalyst. The metal may comprise a transition metal. In a further embodiment, the metal may comprise platinum, palladium, iridium, rhenium, ruthenium and mixtures thereof. The metal may be a noble metal. In an additional embodiment, a modifier metal may also be included on the catalyst. The modifier metal may include tin, germanium, gallium, indium, thallium, zinc, silver and mixtures thereof. The modifier metal should be more concentrated on the binder than on the zeolite. In an embodiment, about 0.01 to about 5 wt % of each of the transition metal and the modifier metal are on the catalyst. The catalyst may comprise about 0.1 to about 3 wt % transition metal.

Metal may be incorporated into the binder by evaporative impregnation. A solution of platinum such as tetraamine platinate nitrate or chloroplatinic acid may be contacted with the spheric supports which have been calcined and ion-exchanged in a rotary evaporator, followed by drying and oxidation.

In a preferred embodiment, the NEP catalyst comprises a metal on the spheric supports of the catalyst. Preferably, more of the metal is on the binder than on the zeolite. In an embodiment, at least 60 wt %, suitably at least 70 wt %, preferably at least 80 wt % and most preferably at least 90 wt % of the metal is on the binder. In an embodiment, the zeolite and/or the entire NEP catalyst is steamed oxidized to drive the metal off the zeolite. Steaming is preferably effected after the metal is added to the catalyst. The dried, metal-impregnated binder supports may be steam oxidized in air for sufficient time to provide NEP catalysts. Steam oxidation in air at a temperature of about 500° C. to about 650° C. and about 10 mol % to about 30 mol % steam for about 1 to 3 hours may be suitable.

The NEP catalysts are preferably reduced to activate them for catalyzing the NEP reaction. For example, the catalyst may be reduced in flowing hydrogen at about 500 to about 550° C. for about 2 to about 5 hours before contacting feed.

After paraffin conversion, a light paraffin stream is discharged from the NEP reactor 16 in an effluent line 18. The light paraffin stream may comprise at least about 40 wt % ethane or at least about 40 wt % propane or at least about 70 wt % and preferably at least about 80 wt % ethane and propane. The ethane to propane ratio can range from about 0.1 to about 5. The light paraffin stream can have less than about 15 wt %, suitably less than about 12 wt %, more suitably less than about 10 wt %, preferably less than about 8 wt %, more preferably less than about 6 wt % and most preferably less than about 5 wt % methane.

We have found that the presence of sulfur in the NEP reaction does not significantly impact conversion. At least about 200 wppm sulfur can be present in the feed without significant impact on conversion. We expect that the NEP catalyst can handle as much as about 400 and perhaps about 500 wppm sulfur without significant impact on conversion.

The light paraffin stream may be cooled and fed to an NEP separation unit 20. The NEP separation unit 20 may be a fractionation column or a series of fractionation columns and other separation units that may separate the light paraffin stream in line 18 into the hydrogen stream in line 22, an ethane stream in line 24, a propane stream in line 26 and the heavy stream in line 12. The NEP separation unit 20 may comprise a demethanizer column that separates the light paraffin stream into a gas stream in an overhead line and a C2+ paraffin stream in a bottoms line. The gas stream may be sent to a hydrogen purification unit such as a PSA unit to recover hydrogen in line 22 for recycle to the NEP reactor 16. Remaining methane from the hydrogen purification unit may be used for fuel gas. The C2+ paraffin stream may then be fed to a deethanizer column to produce the ethane stream in a deethanizer overhead line 24 and a C3+ paraffin stream in a deethanized bottoms line. The C3+ paraffin stream may then be fed to a depropanizer column to produce the propane stream in a depropanizer overhead line 26 and the heavy paraffin stream in the recycle line 12 which may comprise C4+ hydrocarbons. The NEP separation unit 20 may take other forms.

For example, the NEP separation unit 20 may omit a demethanizer column and the light paraffin stream in line 18 may feed a deethanizer column which produces a C2– stream in a deethanizer overhead line. The C2– stream can be separated in the hydrogen purification unit to recover a hydrogen stream in line 22 while residual ethane and methane from the hydrogen purification unit can comprise or supplement the ethane stream in line 24. The hydrogen purification unit may comprise a membrane unit and the hydrogen recovered from the membrane unit may be further purified in an absorption column before it is recycled to the NEP reactor 16 in line 22. In an additional alternative, the C2– stream from the deethanizer column may be charged to an ethylene producing unit 30 in which ethane is converted to ethylene but methane and hydrogen rides through inertly to be recovered in a downstream ethylene recovery unit.

The ethane stream in line 24 may be charged to an ethylene producing unit 30 in which ethane in the ethane stream is converted into ethylene. In an embodiment, ethylene producing unit 30 is a steam cracking unit. The ethane stream in line 24 may be cracked under steam in a furnace to produce a cracked stream including an ethylene stream 32. The ethane stream may be charged to the ethane steam cracking unit in the gas phase. The ethane steam cracking unit may preferably be operated at a temperature of about 750° C. (1382° F.) to about 950° C. (1742° F.). The cracked stream exiting the furnace of the ethane steam cracking unit may be in a superheated state. One or more quench columns, or other devices known in the art, but preferably an oil quench column and/or a water quench column, may be used for quenching or separating the cracked stream into a plurality of cracked streams. The ethane steam cracking unit may further comprise additional distillation columns, amine wash columns, compressors, expanders, etc. to separate the cracked stream into cracked streams rich in individual light olefins the most predominant of which is the ethylene stream in line 32. The ethylene stream may comprise a yield of at least 75 wt %, preferably at least 80 wt %, ethylene based on the ethane stream in line 24. Among the other components in the cracked stream exiting the ethane steam cracking, ethylene producing unit 30 may be hydrogen, methane, propylene, butene, and pyrolysis gas. Each of these components may be recovered and further processed.

The ethylene stream in line 32 and a propylene stream from the ethylene producing unit 30 may be recovered or transported to polymerization plants, chemical plants or exported. A butene stream may be recovered and used to produce plastics or other petrochemicals by processes such as polymerization or exported. Product recovery of at least 50 wt %, typically at least 60 wt % and suitably at least 70 wt % of valuable ethylene, propylene, and butylene products is achievable from the ethane steam cracking unit 30 based on the ethane stream in line 32.

In another embodiment, the ethylene producing unit 30 may be an oxidative dehydrogenation (ODH) unit. The ethane stream in line 24 may be charged to the ODH unit. An ethane ODH process is an alternative technology to ethane steam cracking or ethane pyrolysis for the conversion of ethane into ethylene. Ethane ODH involves contacting an ethane feed and an oxygen source in the presence of an ODH catalyst in an ODH reaction zone under conditions to oxidatively dehydrogenate at least a portion of the ethane to produce a product stream comprising ethylene, carbon oxides, water, and unreacted oxygen, acetic acid and other organic acids and unconverted ethane. The oxygen source can be an oxygen containing stream or an oxygen containing material such as a metal oxide. Mixed-metal-oxide catalysts have been found to be effective for oxidative dehydrogenation reactions.

The ODH reactor may use a mixed-metal oxide catalyst and operate at temperatures of about 300 to about 400° C. and produce over 90% ethylene and acetic acid, both useful products. The ODH unit produces the ethylene stream in line 32 along with an acetic acid stream. Ethane oxidative dehydrogenation using the mixed-metal oxide catalysts may be carried out at a temperature from about 300° C. to about 500° C., preferably from about 350° C. to about 450° C. at a pressure of from about 0.1 to about 20 barg, preferably from about 0.1 to about 10 barg, a space velocity of from about 1000 to about 5000 cm3/(gcat·hr), wherein the molar ratio of ethane to oxygen is about 1.5:1 to 2:1 with sufficient inert diluent to achieve safe operating conditions. MoVNbTe-oxide catalysts (and other related materials) with the M1-type structure are believed to be the best catalysts for ethane ODH.

Ethane ODH using a mixed-metal oxide catalyst in which the catalyst is also the oxygen source may be carried out at a temperature from about 600° C. to about 900° C., preferably from about 750° C. to about 850° C. at a pressure of from about 0.1 to about 20 barg, preferably from about 0.1 to about 10 barg, and a gas hourly space velocity of from about 1000 to about 5000 h-1. Mg6MnO8-oxide catalysts (and other related materials) have been identified as preferable materials for ethane ODH processes in which the catalyst is also the oxygen source.

The propane stream in line 26 may be charged to a propylene producing unit 40 in which propane in the propane stream is converted into propylene. The propylene producing unit 40 may be a paraffin dehydrogenation (PDH) unit. PDH catalyst is used in a dehydrogenation reaction process to catalyze the dehydrogenation of paraffins, such as propane. The conditions in the dehydrogenation reactor may include a temperature of about 500 to about 800° C., a pressure of about 40 to about 310 kPa and a catalyst to oil ratio of about 5 to about 100.

The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated in a regenerator. The regenerator may combust coke from the dehydrogenation catalyst and fuel gas to ensure sufficient enthalpy in the dehydrogenation reactor to promote the endothermic reaction.

The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An exemplary embodiment of a catalyst includes alumina or silica-alumina containing gallium, a noble metal, and an alkali or alkaline earth metal.

The catalyst support comprises a carrier material, a binder and an optional filler material to provide physical strength and integrity. The carrier material may include alumina or silica-alumina. Silica sol or alumina sol may be used as the binder. The alumina or silica-alumina generally contains alumina of gamma, theta and/or delta phases. The catalyst support particles may have a nominal diameter of about 400 to about 5000 micrometers with the average diameter of about 600 to about 3500 micrometers. Preferably, the surface area of the catalyst support is about 85 to about 140 m2/g.

The fluidized dehydrogenation catalyst may comprise a dehydrogenation metal on a support. The dehydrogenation metal may be a one or a combination of transition metals. A noble metal may be a preferred dehydrogenation metal such as platinum or palladium. Gallium is an effective metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.001% to 10 wt % metals may be incorporated into the dehydrogenation catalyst. In the case of the noble metals, it is preferred to use about 10 parts per million (ppm) by weight to about 600 ppm by weight noble metal. More preferably it is preferred to use about 10 to about 100 ppm by weight noble metal. The preferred noble metal is platinum. Gallium should be present in the range of 0.3 wt % to about 3 wt %, preferably about 0.5 wt % to about 2 wt %. Alkali and alkaline earth metals may be present in the range of about 0.05 wt % to about 1 wt %.

Regenerated catalyst may be contacted with the propane stream in line 26 perhaps with a fluidizing gas to lift the propane stream and dehydrogenation catalyst up a riser while dehydrogenation occurs. Above the riser spent dehydrogenation catalyst and propylene product may be separated by a centripetal separation device. Propylene product gas may be quenched with a cooling fluid to prevent over reaction to undesired by-products. Separation of the propylene product may include quench contacting and fractionation to produce a propylene product stream in line 42. Unreacted propane may be recycled to the dehydrogenation reactor and lighter gases may be recycled to the regenerator as fuel gas to be combusted to provide enthalpy for the reaction.

The propylene producing unit may also employ a catalytic moving bed reactor. The reactor section may comprise several radial flow reactors in parallel or series heated by charge and interstage heaters. The propane stream perhaps with added hydrogen flows in each dehydrogenation reactor from a screened center pipe through an annular dehydrogenation catalyst bed to an outer effluent annulus. Flow may be in the reverse fashion. The dehydrogenation catalyst may comprise a noble metal or mixtures thereof, a modifier selected from the group consisting of alkali metals or alkaline-earth metals and mixtures thereof, a component selected from the group consisting of tin, germanium, lead, indium, gallium, thallium, and mixtures thereof, and a porous support forming a catalyst particle. The catalyst support may comprise oil dropped alumina spheres.

Dehydrogenation conditions may include a temperature of from about 400 to about 900° C., a pressure of from about 0.01 to 10 atmospheres absolute, and a liquid hourly space velocity (LHSV) of from about 0.1 to 100 hr-1. The pressure in the dehydrogenation reactor is maintained as low as practicable, consistent with equipment limitations, to maximize chemical equilibrium advantages. Spent dehydrogenation catalyst in the annular catalyst bed may be withdrawn from the bottom of the bed, forwarded to a regenerator to combust coke from the catalyst with air at about 450 to about 600° C. Noble metal on the catalyst may be redispersed by an oxyhalogenation process, dried and returned to the top of the dehydrogenation catalyst bed as regenerated dehydrogenation catalyst.

Dehydrogenation effluent from the propylene producing unit 40 may be cooled, compressed, dried and hydrogen is cryogenically separated from the hydrocarbons with a net gas purity of 85 to 93 mol % hydrogen. Hydrocarbon liquid is selectively hydrogenated to convert diolefins and acetylenes and the hydrocarbon liquid is fractionated in a deethanizer column to remove ethane and propylene is split from propane in a propane-propylene splitter column to provide polymer-grade propylene in line 42. Propane may be recycled as feed to the propylene producing unit 40.

The heavy stream in line 12 which may be taken from a bottom of a depropanizer column may comprise C4+ paraffins. The heavy stream in line 12 may be recycled to the NEP reactor 16 by combination with the paraffin stream in line 10 and the hydrogen stream in line 22 and charged to the NEP reactor in line 11 to produce more ethane and propane.

In an alternative embodiment, the light paraffin stream in line 18 may be separated by the NEP separation unit 20 into a hydrogen stream in line 22, an ethane stream in line 24 and a heavy stream in line 12 as previously described, but the propane stream in line 26 can include isobutane. In this embodiment, a propane and isobutane stream in line 26 can be fed to the propylene producing unit 40. The propylene producing unit 40 can be equipped to dehydrogenate propane in the propane and isobutane stream 26 to propylene and isobutane in the propane and isobutane stream in line 26 to isobutylene in the same dehydrogenation reactor(s). The fractionation section from the propylene producing unit 40 may include a depropanizer column downstream of the bottoms line of the propylene-propane splitter column to separate unreacted propane in an overhead from C4 hydrocarbons. An isobutylene-isobutane splitter column in downstream communication with a bottom of the depropanizer column may provide isobutylene in the overhead that can be recovered as product and unreacted isobutane in the splitter bottoms may be returned to the propylene producing unit 40 to be converted to isobutylene.

Unreacted normal C4+ hydrocarbons comprising normal C4 and higher paraffins in the heavy stream 12 may be recycled to be combined with the naphtha stream in the feed line 10 and the hydrogen stream in line 22 and charged to the NEP reactor 16 in line 11.

Figure 2:
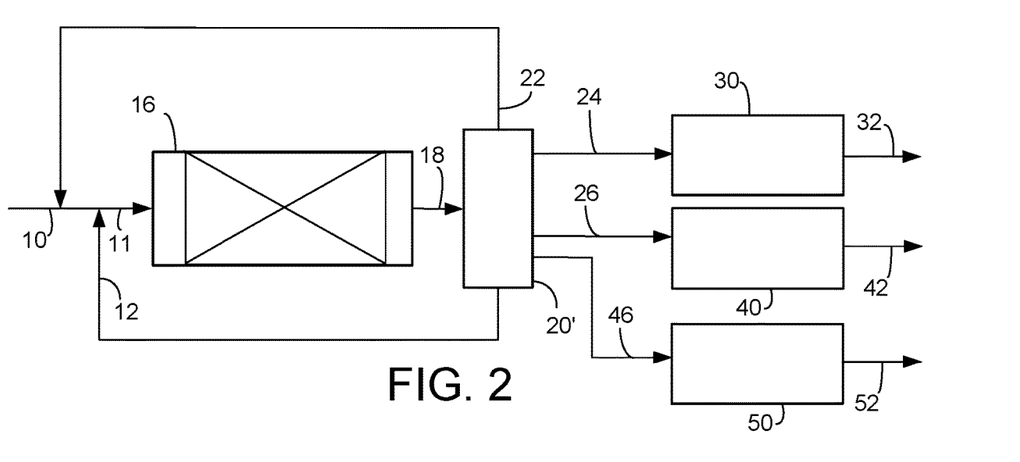
FIG. 2 is a schematic drawing of a process and apparatus of an alternative embodiment of FIG. 1.

FIG. 2 shows an embodiment of an alternative embodiment to the embodiment of FIG. 1 which employs a normal butylene conversion unit 50. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a prime symbol ('). The configuration and operation of the embodiment of FIG. 2 is essentially the same as in FIG. 1 with the following exceptions.

The NEP separation unit 20' additionally provides a normal butane product stream in line 46 in addition to the hydrogen stream in line 22, the ethane stream in line 24 and the propane and isobutane stream in line 26. The normal butane stream in line 46 may be charged to a butylene producing unit 50 for conversion of the normal butane in the normal butane stream to normal butylene. This embodiment may be useful in cases in which the propylene producing unit cannot process propane and normal butane in the same dehydrogenation reactor. The butylene producing unit 50 may include a dehydrogenation unit as described for the propylene producing unit in the embodiment of FIG. 1.

The butylene producing unit 50 may feed a normal butylene stream to a normal butylene-normal butane splitter column. A normal butylene stream in a splitter overhead line may be taken as normal butylene product in line 52 while the unreacted normal butane in the bottoms line may be recycled back to the dehydrogenation unit in the butylene producing unit 50 to be converted to normal butylene.

In some cases, the butylene producing unit 50 may be a butylene producing unit that is able to convert both normal butane and isobutane to normal butene and isobutene. In such a case, the line 46 will carry a butane stream which is lean of propane to a butylene producing unit 50 and the propane stream in line 26 will carry a propane stream that is lean in butane to the propylene producing unit. The butylene producing unit will produce a butene product stream in line 52 that may comprise isobutene and butene.

The heavy stream in line 12 from the NEP separation unit 20' may comprise a C5+ hydrocarbon stream although it may include C4 hydrocarbons and comprise a C4+ hydrocarbon stream. Unreacted C4+ or C5+ hydrocarbons comprising C4 or C5 and heavier hydrocarbons in the heavy stream 12 may be recycled to be combined with the naphtha stream in the feed line 10 and the hydrogen stream in line 22 and charged to the NEP reactor 16 in line 11.

Figure 3:
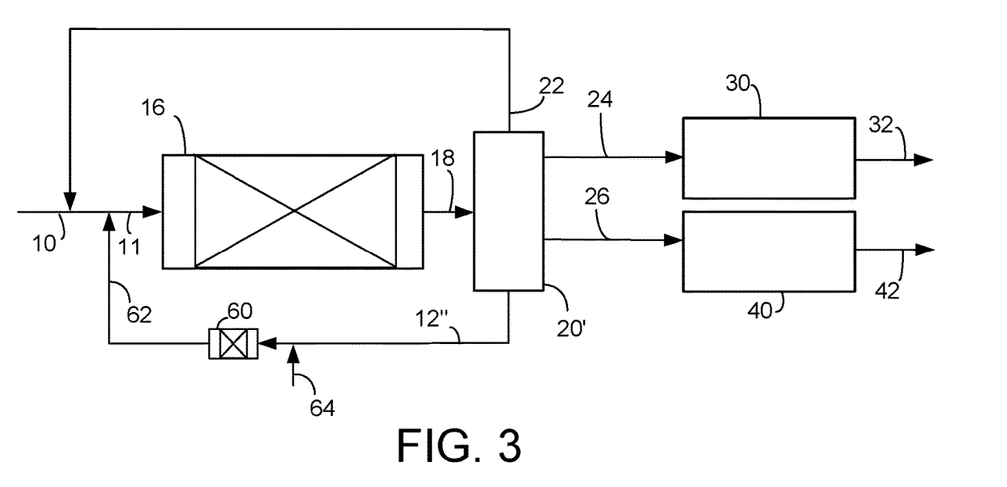
FIG. 3 is a schematic drawing of a process and apparatus of an additional alternative embodiment of FIG. 1.

We have also found that the heavy paraffin stream in line 12 may also comprise aromatics, benzene, toluene and xylene. FIG. 3 shows an embodiment of an alternative embodiment to the embodiment of FIG. 1 which maximizes ethane and propane production by hydrotreating the entire heavy stream in line 12" in a hydrotreating reactor 60 to saturate aromatic rings to naphthenes providing a recycle feed in line 62 to the NEP reactor 16. Elements in FIG. 3 with the same configuration as in FIG. 1 will have the same reference numeral as in FIG. 1. Elements in FIG. 3 which have a different configuration as the corresponding element in FIG. 1 will have the same reference numeral but designated with a double prime symbol ("). The configuration and operation of the embodiment of FIG. 3 is essentially the same as in FIG. 1 with the following exceptions.

The heavy stream in line 12" comprising C4+ paraffins and aromatics, benzene, toluene and xylene is mixed with a hydrogen stream in line 64, heated and charged to the hydrotreating reactor 60.

The hydrotreating reactor 60 may have one or more beds of hydrotreating catalyst to saturate aromatic rings in the heavy stream. The heavy stream may be charged to the hydrotreating reactor 60 at a hydrotreating inlet temperature that may range from about 200° C. (392° F.) to about 400° C. (752° F.). The hydrotreating reactor 60 may employ interbed hydrogen quench streams if more than one catalyst bed is used.

Suitable hydrotreating catalysts are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present description that more than one type of hydrotreating catalyst be used in the same hydrotreating reactor 60. The Group VIII metal is typically present in an amount ranging from about 2 to about 20 wt %, preferably from about 4 to about 12 wt %. The Group VI metal will typically be present in an amount ranging from about 1 to about 25 wt %, preferably from about 2 to about 25 wt %. Generally, hydrotreating conditions include a pressure of about 700 kPa (100 psig) to about 21 MPa (3000 psig). The hydrotreating outlet temperature may range between about 300° C. (572° F.) and about 427° C. (800° F.).

The saturated aromatics and C4+ paraffins in a hydrotreated heavy stream in line 62 may be recycled to join the naphtha stream in line 10 and the hydrogen stream in line 22 and be charged to the NEP reactor 16 in line 11. Hydrogen from the hydrotreating reactor 60 may be recycled with the saturated aromatics to the NEP reactor 16 to reduce or eliminate hydrogen requirements from line 22.

Figure 4:
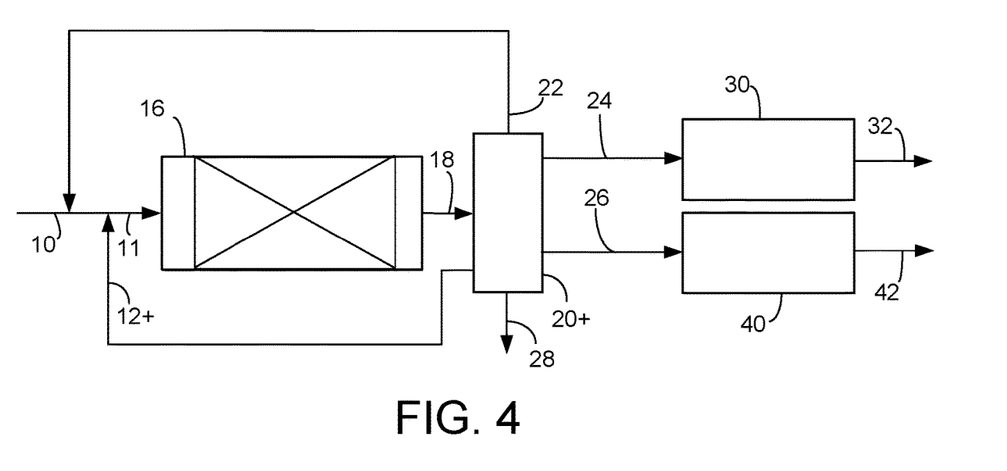
FIG. 4 is a schematic drawing of a process and apparatus of a further alternative embodiment of FIG. 1.

In another embodiment, the NEP separation unit 20+ includes a debutanizer column that separates C4 and perhaps C5 hydrocarbons for recycle to the NEP reactor 16 in line 12+ while preserving aromatics for further processing and valorization. FIG. 4 shows an alternative embodiment to the embodiment of FIG. 1 which preserves aromatics. Elements in FIG. 4 with the same configuration as in FIG. 1 will have the same reference numeral as in FIG. 1. Elements in FIG. 4 which have a different configuration as the corresponding element in FIG. 1 will have the same reference numeral but designated with a cross symbol (+). The embodiment of FIG. 4 operates and is configured essentially as FIG. 1 with the following exceptions.

The NEP separation unit 20+ includes a debutanizer column that separates a heavy stream comprising C4 and perhaps C5 paraffins from a depropanizer bottoms stream in a debutanizer overhead line for recycle to the NEP reactor 16 in line 12+ and C5+ or C6+ aromatics in a debutanized bottoms line 28. The aromatics in the debutanized bottoms line 28 may be further processed for valorization of the valuable aromatics. The The foregoing disclosure provides a process for converting naphtha to ethane and propane feed with maximized conversion to ethylene and propylene in ethylene and propylene producing units, respectively.

EXAMPLES

Example 1

Zeolite MFI with a $Si/Al_2$ ratio of 40 was synthesized by crystallizing a mixture consisting of silica, alumina, alkali metal and an OSDA comprising tetrapropyl ammonium (TPA). As synthesized zeolite MFI was first mixed with $AlPO_4$ sol and gelling reagent, and the formed slurry was dropped into hot oil. The size of the spheres was controlled to attain $\frac{1}{16}$-inch diameter calcined support. The formed spheres coming off sphere forming section was separated from the oil and transported to the washing section for ammonia wash to remove sodium ions off the zeolite. The wet spheres were dried and then calcined to remove the OSDA. Optionally the calcined support is $NH_4$-ion exchanged using an ammonium nitrate solution to remove residual sodium ions, followed by a drying step at about 110° C. prior to a metal incorporation step. Platinum incorporation was performed by an evaporative impregnation technique via contacting the supports with a solution of platinum containing compounds such as tetraamine platinate nitrate in a rotary evaporator, followed by drying with heat introduced from a steam jacket. Once the spheres become free rolling, the impregnated support was steam oxidized at 607° C. with 14.3 mol % steam in flowing air for 2 hours in a quartz tube in a 3-zone furnace. The levels of platinum on the finished catalysts were 0.02 wt % and 0.40 wt % and are designated as Examples 1.1 and 1.2, respectively.

Example 2

An alternative preparative sequence to Example 1.2 was employed by first calcining $AlPO_4$-bound oil dropped spheres, which were ammonium-ion exchanged to remove residual sodium and then steam calcined using 14.3 mol % steam at 607° C. for 2 hours. The steam calcined supports were evaporatively impregnated with a solution of tetraamine platinate followed by dry oxidation at 520° C. for 2 hours in flowing air. The catalyst contained 0.4 wt % platinum and is designated as Comparative Example 2.

Example 3

A series of catalysts containing 0, 0.005, 0.02, 0.1 and 0.4 wt % platinum on $AlPO_4$-bound MFI with a $Si/Al_2$ ratio of 40 were prepared following the procedure described in Example 1 with the exception that 7.7 wt % instead of 14.3 wt % steam was co-fed during the steam oxidation step. The catalysts are designated as Examples 3.1, 3.2, 3.3, 3.4 and 3.5.

Example 4

An extrudate of 1/16-inch cylindrical shape was prepared with a formulation of 65% MFI-40 prepared according to that in Example 1, 20% Hisil 532 $SiO_2$ and 15% Ludox AS-40 $SiO_2$. An extrusion aid of 1% Methocel A was incorporated into the formulation. The extrudate was dried at 110° C., calcined at 520° C. over a flowing air in a muffle oven. The calcined support was ammonium ion exchange using 1.0 M of ammonium nitrate solution to remove residual sodium. The ammonium ion exchange support was dried at 110° C. and tetraamine platinate was subsequently incorporated onto the support by evaporative impregnating technique to attain either 0.2 or 0.4% platinum on the finished catalysts. The impregnated support was steam oxidized at 607° C. and 14.3% steam for 2 hours and the finished catalyst is designated as Example 4.1 and 4.2, respectively.

In one preparative permutation the impregnated support of 0.2 wt % platinum was oxidized in dry flowing air at 520° C. for 2 hours and designated as catalyst Comparative Example 4.3.

In another preparative permutation the impregnated support of 0.2 wt % platinum was prepared using chloroplatinic acid instead of tetraamine platinate nitrate, followed by steam oxidation at 607° C. and 14.3% steam for 2 hours, and designated as catalyst Example 4.4.

Example 5

In an example of preparing zirconia-bound zeolitic catalyst, 366 g of zirconyl hydroxynitrate (ZHN) or ZrO(OH)(NO3) solution, was mixed with 202 g water and cooled to 10 to 15° C. Subsequently, 60 g of pre-cooled gelling reagent made up 42% hexamethylene tetraamine (HMT) solution was added with vigorous stirring at 10° C. The solution was then added to a ball mill. Thereafter, 229 g of H-MFI-Q powder was added to the ball mill containing the aforementioned solution, and the resulting slurry was ball milled for 30 minutes. The slurry was then dropped into 95° C. oil to form gelled spheres, which were kept in the hot oil for two hours to age at 95° C. The aged spheres were then transferred to a wash column and the oil was displaced with $NH_4NO_3$ at 95° C. for over 30 minutes. Spheres were then washed in same column with $NH_4NO_3$ solution pH adjusted with $NH_4OH$ at 95° C. for one hour. Spheres were then dried overnight at 95° C. The oil dropped spheres were further dried at 110° C. for 2 hours, and then calcined at 560° C. for 4 hours. The calcined support was evaporatively impregnated with a solution of chloroplatinic acid (CPA) or tetraamine platinate nitrate (TAPN), followed by either oxidation at 520° C. in flowing dry air or oxidation at 607° C. in flowing air containing 14.3 molar percentage of moisture, respectively. They are labelled as catalyst Examples 5.1 (CPA-dry oxid), 5.2 (CPA, steam oxid), 5.3 (TAPN, dry oxid) and 5.4 (TAPN, steam oxid).

Example 6

A MFI-40 material synthesized according to that described in Example 1 was mixed with silica sol, and the resulting mixture was dropped into a hot oil bath via a vibrating tip to form spheres. The spheres were aged, water washed, dried and calcined in flowing air. Platinum was incorporated onto the support via evaporative impregnation using a tetraamine platinate nitrate solution to attain 0.02 wt % platinum on the finished catalyst and subsequently oxidized at 500° C. for 4 hours in flowing air. The catalyst is designated as catalyst Example 6.1. A related catalyst was prepared using Silicalite zeolite of 500 $Si/Al_2$ ratio. Platinum was incorporated onto the support via evaporative impregnation using a tetraamine platinate nitrate solution to attain 0.1 wt % platinum on the finished catalyst and subsequently pelletized into 20×60 mesh and oxidized at 500° C. for 4 hours in flowing air. The catalyst is designated as catalyst Example 6.2.

Example 7

Molecular sieve AEL or SAPO-11 was obtained from Clariant. The composition is 23.2 aluminum, 22.2 phosphorous and 2.73 silicon with 256 $m^2/g$ BEA surface area, 0.11 ml/g micropore volume and 0.21 ml/g total pore volume as per nitrogen adsorption measurement. The molecular sieve was extruded with alumina binder into 70/30 SAPO-11/$Al_2O_3$ formulation into 1/16-inch diameter cylinders and subsequently finished with chloroplatinic acid to attain 0.25 wt % platinum on the finished catalyst.

Example 8

A catalytic test was performed upon Catalyst Example 1.1 in a plug flow tubular reactor. The finished catalyst was crushed and 1 gram of catalyst at 20×60 mesh was premixed with 3 grams of sand, before it was loaded in the reactor. The composition of the feed blend is shown in Table 2, mimicking that of light naphtha. The feed was further spiked with di-methyl disulfide and thiophene to attain a total sulfur content of 200 wppm. The catalyst was pre-reduced at 520° C. for 3 hours in a flowing hydrogen stream, and then lowered to the target reaction temperature, before the feed was introduced. At temperatures of about 400 to about 430° C., a WHSV of about 4.0 to about 8.0, a hydrogen-to-hydrocarbon molar ratio of around 1.0 and a total pressure of about 200 psig, 13.8 bars (gauge), it can be seen at in Table 2 that the total amount of C2-C4 is consistently in an excess of 80% and the total amount of C2-C3 is consistently in an excess of 70% over a broad range of contact times in terms of space velocity, while keeping methane at less than about 5 wt-%. Furthermore, out of the C2-C4 produced, more than 50 wt-% is C3. The amounts of ethane can be increased via increased temperatures, while maintaining propane yields at about 60 wt-%. Conversion is calculated as the ratio of C3− hydrocarbons and aromatics in the product to the C4+ hydrocarbons and non-aromatics in the feed.

TABLE 2

|  | Feed | Example 1.1: 0.02% Pt on MFI(40)/AlPO$_4$ | | | | | |
|---|---|---|---|---|---|---|---|
| Feed S, wppm |  | 200 | 200 | 200 | 200 | 200 | 200 |
| Temp, °C. |  | 400 | 421 | 421 | 421 | 421 | 431 |
| P(light naphtha), psia (bars) |  | 107 (7.4) | 107 (7.4) | 108 (7.5) | 107 (7.4) | 119 (8.2) | 97 (6.7) |
| P(hydrogen), psia (bars) |  | 108 (7.5) | 108 (7.5) | 108 (7.5) | 108 (7.5) | 96 (6.6) | 117 (8.1) |
| WHSV, hr$^{-1}$ |  | 6.0 | 6.0 | 8.0 | 4.0 | 6.0 | 6.0 |
| Hours on Stream |  | 8.6 | 13.6 | 15.6 | 20.6 | 29.7 | 36.7 |
| C4-C9 naphtha conversion |  | 80.22 | 87.58 | 84.78 | 89.99 | 88.77 | 88.54 |
| Yields, wt % |  |  |  |  |  |  |  |
| C1 |  | 2.39 | 4.12 | 3.92 | 4.27 | 4.10 | 5.02 |
| C2 |  | 12.65 | 17.49 | 17.14 | 17.36 | 16.83 | 19.34 |
| C3 |  | 60.44 | 60.64 | 59.34 | 61.04 | 60.99 | 58.73 |
| C4s |  | 17.19 | 11.47 | 13.77 | 9.23 | 10.33 | 10.67 |
| nC5 | 24.12 |  |  |  |  |  |  |
| iC5 | 11.88 |  |  |  |  |  |  |
| nC6 | 25.44 |  |  |  |  |  |  |
| iC6 | 21.53 |  |  |  |  |  |  |
| Cyclohexane and Methylcyclopentane | 15.03 |  |  |  |  |  |  |
| C7-C9 naphtha | 2 |  |  |  |  |  |  |
| Aromatics |  | 4.59 | 5.17 | 4.33 | 6.98 | 6.58 | 5.30 |
| Heavies |  | 0.15 | 0.16 | 0.11 | 0.34 | 0.27 | 0.15 |
| C2/C3 weight ratio |  | 0.2093 | 0.28842 | 0.28884 | 0.2844 | 0.27595 | 0.3293 |

Example 9

The test described in Example 8 was switched to a feed blend that does not contain sulfur. Under comparable test conditions, the catalyst exhibited performance comparable to that with the sulfur containing feed blend as shown in Table 3. For example, the performance results obtained using sulfur containing feed at 13.6 hours on stream are comparable to those obtained using sulfur-free feed at 120.6 and 124.6 hours on stream. Also increasing the temperatures would allow tuning the ethane production, while maintaining propane production around 60% yields. It is noted that by increasing the contact times by lowering WHSV, one can reach 65% propane yields at lower temperatures, while keeping methane production at less than 3%.

Example 10

The catalyst of Example 1.1 was tested following the same protocol described in Example 8. The test was performed by varying hydrogen-to-hydrocarbon molar ratios, while fixing the pressures around 200 psig, 13.8 bars (gauge). It was observed that about 80 wt % of C2 to C4 and greater than 70% of C2 to C3 were produced in each run as shown in Table 4. Also, ethane made up more than 60 wt % of the total C2 to C3 and C2 to C4 as hydrogen-to-hydrocarbon ratios were reduced to below about 5.0. Furthermore, ethane make-up was further increased with the increased contact times by lowering WHSV. The increased ethane production was also accompanied by lower methane and increased valuable aromatics production.

TABLE 3

|  | Feed | Example 1.1: 0.02% Pt on MFI(40)/AlPO$_4$ with no Sulfur | | | | | | | |
|---|---|---|---|---|---|---|---|---|---|
| Feed S, wppm |  | 0 | 0 | 0 | 0 | 0 | 0 | 0 | 0 |
| Temp, °C. |  | 421 | 421 | 421 | 431 | 431 | 421 | 411 | 400 |
| P(light naphtha), psia |  | 107 (7.4) | 98 (6.8) | 119 (8.1) | 107 (7.4) | 107 (7.4) | 106 (7.3) | 106 (7.3) | 106 (7.3) |
| P(hydrogen), psia |  | 108 (7.5) | 117 (8.1) | 96 (6.6) | 108 (7.5) | 108 (7.5) | 109 (7.5) | 109 (7.5) | 109 (7.5) |
| WHSV, hr$^{-1}$ |  | 3.9 | 5.9 | 5.9 | 5.9 | 3.9 | 1.9 | 1.9 | 1.9 |
| Hours on Stream |  | 116.6 | 120.6 | 124.6 | 128.6 | 135.6 | 148.6 | 154.6 | 159.6 |
| C4-C9 naphtha conversion |  | 89.90 | 83.55 | 87.33 | 89.08 | 92.20 | 92.16 | 90.25 | 87.27 |
| Yields, wt % |  |  |  |  |  |  |  |  |  |
| C1 |  | 4.17 | 3.68 | 4.14 | 5.25 | 5.89 | 4.80 | 3.49 | 2.52 |
| C2 |  | 17.57 | 16.57 | 17.43 | 20.44 | 21.88 | 21.40 | 16.85 | 13.50 |
| C3 |  | 62.55 | 59.32 | 61.05 | 59.19 | 59.29 | 59.17 | 63.45 | 65.11 |
| C4s |  | 9.48 | 15.32 | 11.96 | 10.50 | 7.50 | 7.28 | 9.04 | 11.66 |
| nC5 | 24.12 |  |  |  |  |  |  |  |  |
| iC5 | 11.88 |  |  |  |  |  |  |  |  |
| nC6 | 25.44 |  |  |  |  |  |  |  |  |
| iC6 | 21.53 |  |  |  |  |  |  |  |  |
| Cyclohexane and Methylcyclopentane | 15.03 |  |  |  |  |  |  |  |  |
| C7-C9 naphtha | 2 |  |  |  |  |  |  |  |  |
| Aromatics |  | 5.44 | 3.90 | 4.58 | 4.12 | 4.99 | 6.49 | 6.20 | 5.91 |
| Heavies |  | 0.17 | 0.08 | 0.11 | 0.09 | 0.14 | 0.31 | 0.26 | 0.22 |
| C2/C3 weight ratio |  | 0.281 | 0.279 | 0.286 | 0.3453 | 0.3690 | 0.3617 | 0.2656 | 0.2073 |

TABLE 4

|  | Feed | Example 1.1: 0.02 wt % Platinum on MFI(40)/AlPO$_4$ | | | | | |
| --- | --- | --- | --- | --- | --- | --- | --- |
| Hours on Stream |  | 90.6 | 94.6 | 98.6 | 102.6 | 106.6 | 110.6 |
| WHSV, hr$^{-1}$ |  | 6.0 | 6.0 | 6.0 | 12.0 | 12.0 | 12.0 |
| H2/HCBN molar ratio |  | 5.0 | 2.0 | 1.2 | 1.2 | 2.0 | 5.0 |
| Temperature, ° C. |  | 495.6 | 495.6 | 494.1 | 497.9 | 502.0 | 502.8 |
| Reactor Outlet Pressure, bars |  | 14.6 | 14.6 | 14.6 | 14.6 | 14.6 | 14.6 |
| C4+ conversion | 0.00 | 98.42 | 98.71 | 99.78 | 96.58 | 97.57 | 96.56 |
| C1 |  | 11.35 | 12.23 | 8.94 | 6.74 | 9.13 | 8.21 |
| C2s |  | 41.44 | 54.87 | 51.13 | 42.49 | 46.79 | 36.15 |
| C3s |  | 40.39 | 22.19 | 21.73 | 32.36 | 33.28 | 48.29 |
| C4s |  | 2.68 | 1.87 | 2.98 | 4.70 | 3.46 | 5.11 |
| n-C5 or C5s | 29.91 | 0.05 | 0.11 | 0.27 | 0.49 | 0.24 | 0.15 |
| n-C6 or C6s | 25.74 | 0.00 | 0.02 | 0.04 | 0.08 | 0.03 | 0.01 |
| Cyclohexane and Methylcyclopentane | 7.1 | 0.00 | 0.00 | 0.01 | 0.05 | 0.03 | 0.00 |
| n-C$_7$ or C$_7$-C$_9$ Non-Aromatic Naphtha | 30.17 | 0.01 | 0.00 | 0.01 | 0.02 | 0.01 | 0.02 |
| Methylcyclohexane | 7.07 | 0.00 | 0.00 | 0.00 | 0.00 | 0.00 | 0.00 |
| 1 Ring Aromatics |  | 3.96 | 8.11 | 13.13 | 12.08 | 6.64 | 2.03 |
| Heavies |  | 0.11 | 0.60 | 1.78 | 1.00 | 0.39 | 0.02 |
| Sum | 99.99 | 100.00 | 100.00 | 100.02 | 100.00 | 100.00 | 100.00 |
| C2/C3 weight ratio |  | 1.03 | 2.47 | 2.35 | 1.31 | 1.41 | 0.75 |

Example 11

Catalyst prepared according to Example 1.2 was tested following the same protocol described in Example 8. The performance evaluation was carried out by varying the total pressures, contact times in terms of WHSV and temperatures from about 480 to about 495° C., while fixing the hydrogen-to-hydrocarbon molar ratios at around 2.0. It was evident that with reduced total pressures, one can attain greater than about 60 wt % ethane out of total C$_2$ to C$_4$ and less than about 10% of methane, while maintaining about 80% C$_2$-C$_4$ by operating at total pressures of 8 bars or less of naphtha and H$_2$ partial pressures combined.

Example 12

The catalyst of Examples 1.2 and 2 were tested following the same protocol as described in Example 8. The steamed oxidation performed after platinum incorporation as in catalyst Example 1.2 provided significantly higher ethane yields (greater than 50%) than catalyst Example 2 prepared by steaming the support, followed by platinum incorporation and then dry oxidation. Also, the total C$_2$ to C$_3$ produced by catalyst Example 1.2 were higher than 80 wt % with C$_2$ comprising over 60 wt % of the C$_2$ and C$_3$ aggregate with less than 8 wt % and less than 6 wt % methane yield. By

TABLE 5

|  | Feed | Example 1.2: 0.4% Platinum on MFI(40)/AlPO$_4$-steam | | | | | | | | | |
| --- | --- | --- | --- | --- | --- | --- | --- | --- | --- | --- | --- |
| Feed S, wppm |  | 0.00 | 0.00 | 0.00 | 0.00 | 0.00 | 0.00 | 0.00 | 0.00 | 0.00 | 0.00 |
| Hours on Stream |  | 78.8 | 82.8 | 111 | 116 | 123 | 126 | 146 | 152 | 158 | 165 |
| WHSV, hr$^{-1}$ |  | 12.0 | 12.0 | 12.0 | 12.0 | 3.00 | 3.00 | 2.00 | 2.00 | 2.00 | 2.00 |
| H2/HCBN molar ratio |  | 2.00 | 2.00 | 2.00 | 2.00 | 2.00 | 2.00 | 2.00 | 2.00 | 2.00 | 2.00 |
| Temperature, ° C. |  | 494 | 484 | 482 | 493 | 492 | 482 | 482 | 492 | 491 | 482 |
| Reactor Outlet Pressure, bars |  | 14.6 | 14.6 | 20.7 | 20.7 | 7.71 | 7.69 | 4.27 | 4.25 | 2.95 | 2.97 |
| C4-C9 naphtha conversion |  | 96.3 | 95.3 | 95.6 | 96.5 | 97.9 | 97.1 | 97.2 | 98.1 | 97.6 | 96.7 |
| Yields, wt % |  |  |  |  |  |  |  |  |  |  |  |
| C1 |  | 9.45 | 7.91 | 10.5 | 12.0 | 10.9 | 10.1 | 8.04 | 9.49 | 7.36 | 6.06 |
| C2 |  | 50 | 42.1 | 45.5 | 52.6 | 62.6 | 54.6 | 55.6 | 61.3 | 57.3 | 51.6 |
| C3 |  | 32.9 | 42.1 | 36.6 | 28.2 | 20.1 | 29.5 | 29.1 | 22.3 | 26.5 | 33.4 |
| C4s |  | 3.43 | 4.40 | 4.07 | 3.21 | 1.97 | 2.74 | 2.65 | 1.89 | 2.35 | 3.17 |
| nC5 | 24.1 | 0.09 | 0.11 | 0.12 | 0.10 | 0.04 | 0.05 | 0.04 | 0.03 | 0.03 | 0.05 |
| iC5 | 11.9 | 0.14 | 0.17 | 0.18 | 0.16 | 0.05 | 0.07 | 0.05 | 0.04 | 0.04 | 0.06 |
| nC6 | 25.4 | 0.01 | 0.01 | 0.01 | 0.02 | 0.02 | 0.01 | 0.00 | 0.00 | 0.00 | 0.01 |
| iC6 | 21.5 | 0.03 | 0.03 | 0.04 | 0.03 | 0.01 | 0.01 | 0.01 | 0.00 | 0.01 | 0.01 |
| Cyclohexane and Methyl-cyclopentane | 15.0 | 0.01 | 0.02 | 0.01 | 0.01 | 0.00 | 0.00 | 0.00 | 0.00 | 0.00 | 0.00 |
| C7-C9 Naphtha | 2 | 0.00 | 0.00 | 0.01 | 0.00 | 0.00 | 0.00 | 0.00 | 0.00 | 0.00 | 0.00 |
| Aromatics |  | 3.82 | 2.99 | 2.82 | 3.50 | 4.06 | 2.84 | 4.28 | 4.74 | 6.08 | 5.43 |
| Heavies |  | 0.18 | 0.11 | 0.12 | 0.16 | 0.27 | 0.13 | 0.19 | 0.24 | 0.31 | 0.26 |
| Sum | 100 | 100 | 100 | 100 | 100 | 100 | 100 | 100 | 100 | 100 | 100 |
| C2/C3 wt. ratio |  | 1.52 | 1.00 | 1.24 | 1.87 | 3.11 | 1.85 | 1.91 | 2.75 | 2.16 | 1.54 |
| C1/C2 wt. ratio |  | 0.19 | 0.19 | 0.23 | 0.23 | 0.18 | 0.18 | 0.15 | 0.16 | 0.13 | 0.12 | comparison catalyst Example 2 gave lower ethane, lower total $C_2$ to $C_3$ and higher aromatics.

TABLE 6

| | Feed | 20 mol % Steam Oxidation | | Dry Oxidation | |
|---|---|---|---|---|---|
| | | Example | | | |
| | | 1.2 | | 2 | |
| Hours on Stream | | 157.86 | 164.87 | 46.57 | 52.58 |
| Temperature, ° C. | | 491.40 | 481.50 | 481.42 | 490.97 |
| H2/HCBN molar ratio | | 2.00 | 2.00 | 2.13 | 2.08 |
| WHSV, hr$^{-1}$ | | 2.00 | 2.00 | 1.86 | 1.90 |
| Reactor Outlet Pressure, bars | | 2.95 | 2.97 | 3.08 | 3.11 |
| Yields, wt % | | | | | |
| C1 | | 7.36 | 6.06 | 7.25 | 8.87 |
| C2 | | 57.30 | 51.56 | 40.70 | 46.78 |
| C3 | | 26.51 | 33.38 | 37.05 | 28.24 |
| C4s | | 2.35 | 3.17 | 2.67 | 1.97 |
| nC5 | 24.12 | 0.03 | 0.05 | 0.03 | 0.02 |
| iC5 | 11.88 | 0.04 | 0.06 | 0.04 | 0.03 |
| nC6 | 25.44 | 0.00 | 0.00 | 0.00 | 0.00 |
| iC6 | 21.53 | 0.01 | 0.01 | 0.00 | 0.00 |
| Cyclohexane and Methyl-cyclopentane | 15.03 | 0.00 | 0.00 | 0.00 | 0.00 |
| C7-C9 Naphtha | 2 | 0.00 | 0.00 | 0.00 | 0.00 |
| Aromatics | | 6.08 | 5.43 | 11.51 | 13.14 |
| Heavies | | 0.31 | 0.26 | 0.76 | 0.95 |
| Sum | 100.00 | 99.99 | 99.98 | 100.00 | 100.00 |
| C2/C3 ratio | | 2.16 | 1.54 | 1.10 | 1.66 |

Example 13

The catalysts of Examples 3.1 through 3.5 were tested following the similar protocol described in Example 8 using an apparatus made up of multiple, parallel reactors controlled at about 6 bars pressure, a hydrogen-to-hydrocarbon molar ratio of 2.0 over a temperature range of about 390 to about 500° C. About 1 ml of catalyst at 20×60 mesh was loaded into individual reactors with no diluent. The catalyst was pre-reduced at 520° C. for 3 hours, before cooling it down to the first test temperatures and pressuring up to the testing pressures. The results at 480° C. are shown in Table 7.

TABLE 7

| Example | Feed | 3.1 | 3.2 | 3.3 | 3.4 | 3.5 |
|---|---|---|---|---|---|---|
| Platinum, wt % | | 0 | 0.005 | 0.02 | 0.1 | 0.4 |
| WHSV, hr-1 | | 2 | 2 | 2 | 2 | 2 |
| H2/HCBN molar ratio | | 2.0 | 2.0 | 2.0 | 2.0 | 2.0 |
| Temperature, ° C. | | 477.8 | 478.1 | 479.3 | 478.3 | 480.6 |
| Hours on Stream | | 88.6 | 89.0 | 87.8 | 89.4 | 88.2 |
| Reactor Outlet Pressure, bars | | 5.6 | 5.6 | 5.9 | 5.7 | 5.7 |
| C1 | | 2.35 | 7.60 | 8.12 | 7.47 | 7.02 |
| C2 | | 6.35 | 46.62 | 56.80 | 65.76 | 65.08 |
| C3 | | 43.75 | 29.91 | 22.58 | 14.35 | 13.02 |
| C2 + C3 | | 50.10 | 76.53 | 79.38 | 80.11 | 78.11 |
| C4s | | 17.45 | 2.98 | 2.48 | 1.94 | 1.72 |
| C5s | 35.24 | 0.48 | 0.00 | 0.00 | 0.00 | 0.00 |
| C2-C5 olefins | | 6.39 | 0.88 | 0.95 | 1.03 | 1.01 |
| C6s | 47.57 | 12.63 | 0.15 | 0.12 | 0.06 | 0.05 |
| Cyclohexane | 15.64 | | | | | |
| C7s | 1.56 | | | | | |
| Aromatics | | 14.20 | 11.05 | 8.56 | 8.37 | 10.55 |
| A9 | | 1.48 | 0.46 | 0.22 | 0.22 | 0.29 |
| A10 | | 0.32 | 0.00 | 0.00 | 0.00 | 0.00 |

TABLE 7-continued

| Example | Feed | 3.1 | 3.2 | 3.3 | 3.4 | 3.5 |
|---|---|---|---|---|---|---|
| Heavy Aromatics | | 0.97 | 1.22 | 1.12 | 1.85 | 2.27 |
| Sum | 100 | 100.00 | 100.00 | 100.00 | 100.00 | 100.00 |
| C2/(C2-C4), % | | 9.4 | 58.6 | 69 | 80 | 81.5 |

Results show the presence of platinum is required to attain high C2 yield above 40 wt % at around 6 bars pressure, hydrogen-to-hydrocarbon molar ratio of 2.0, a platinum level as low as 50 wppm and 480° C. The presence of platinum is most critical to attain an appreciable yield of $C_2$ above 10 wt %. Increasing platinum content 0.1 wt % and higher elevated levels of $C_2$ yield greater than 60 wt %, while maintaining low levels of methane formation less than 8%. It is further noted that $C_2/C_3$ ratios greater than 5 can be achieved by employing a platinum containing zeolitic catalyst, while maintaining greater than about 80 wt % $C_2$ and $C_3$ combined and less than 8 wt % methane formation.

Example 14

Catalysts prepared according to Examples 4.1 through 4.4 were tested following the test protocol described in Example 14, in which catalysts were tested using a feed simulating light naphtha composition as shown in the Table 8 below in multiple, parallel reactor apparatus using 1 ml of catalyst loading of 20×60 mesh size. The sixth column represents cyclohexane and methylcyclopentane in the feed.

TABLE 8

Simulated Commercial Light Naphtha

| Components | n-C5 | i-C5 | n-C6 | i-C6 | CH & mCP | n-C7 | Sum |
|---|---|---|---|---|---|---|---|
| wt % | 23.09 | 11.54 | 26.40 | 21.10 | 15.82 | 2.05 | 100.00 |

TABLE 9

| Catalysts | Binder | Platinum Precursor | Steam or Dry Oxidation | wt % Pt | H2/Pt | C2 ylds, % | CH4 % |
|---|---|---|---|---|---|---|---|
| Ex. 1.2 | AlPO4 | TAPN | H2O | 0.40 | 0.04 | 54.69 | 5.79 |
| Comp. Ex. 2 | AlPO4 | TAPN | dry | 0.40 | 0.35 | 54.54 | 8.45 |
| Ex. 4.1 | SiO2 | TAPN | H2O | 0.40 | 0.13 | 54.42 | 7.23 |
| Ex. 4.2 | SiO2 | TAPN | H2O | 0.20 | 0.31 | 54.77 | 7.90 |
| Comp. Ex. 4.3 | SiO2 | TAPN | dry | 0.20 | 0.54 | 54.90 | 13.00 |
| Ex. 4.4 | SiO2 | CPA | H2O | 0.20 | 0.13 | 54.95 | 5.59 |

The test results are reported at comparable ethane production levels. $SiO_2$-bound catalyst Example 4.1 gave higher methane formation among the four silica bound catalysts. Catalyst Example 4.4 prepared using chloroplatinic acid as platinum precursor in evaporative impregnation, followed by steam oxidation at 14.4% steam and 607° C. for 2 hours (gave the lowest methane production at about 55% ethane yields. Catalyst example 4.3 prepared using tetraamine nitrate as the platinum precursor in evaporative impregnation, followed by dry oxidation at 520° C. for 2 hours gave significantly higher methane again shown in Table 9.

Example 15

Catalysts prepared according to Examples 5.1 through 5.4 were tested following the test protocol described in Examples 13 and 14, where catalysts were tested using a feed simulating light naphtha composition as shown in the Table 8 in multiple, parallel reactor apparatus using 1 ml of catalyst loading of 20×60 mesh size.

TABLE 10

| Example Catalysts | 1.2 | 5.1 | 5.2 | 5.3 | 5.4 |
|---|---|---|---|---|---|
| Pt Precursor | TAPN | CPA | CPA | TAPN | TAPN |
| Support | AlPO4 | ZrO2 | ZrO2 | ZrO2 | ZrO2 |
| Oxidation | H2O | Dry | H2O | Dry | H2O |
| WHSV_hr$^{-1}$ | 2.0 | 2.0 | 2.0 | 2.0 | 2.0 |
| H2/LN molar | 2.0 | 2.0 | 2.0 | 2.0 | 2.0 |
| Temp., C. | 450.0 | 450.0 | 450.0 | 450.0 | 450.0 |
| Time on stream, hrs. | 70.3 | 69.9 | 68.3 | 69.5 | 68.7 |
| Outlet Pressure, bars | 5.2 | 5.3 | 5.7 | 6.4 | 5.9 |
| Yields, % | | | | | |
| C1 | 4.71 | 4.96 | 4.54 | 5.83 | 4.13 |
| C2s | 41.69 | 56.02 | 37.33 | 52.09 | 30.21 |
| C3s | 41.32 | 26.53 | 47.96 | 26.36 | 51.82 |
| C2s + C3s | 83.01 | 82.55 | 85.29 | 78.46 | 82.03 |
| C4s | 4.79 | 3.17 | 4.64 | 2.81 | 4.64 |
| C5s | 0.00 | 0.00 | 0.00 | 0.00 | 0.00 |
| C2-C5 olefins | 0.75 | 0.48 | 0.66 | 0.50 | 0.54 |
| BTX | 6.11 | 6.57 | 4.30 | 9.54 | 7.73 |
| A9 | 0.13 | 0.25 | 0.11 | 0.28 | 0.13 |
| A10 | 0.00 | 0.00 | 0.00 | 0.00 | 0.00 |
| Heavy Aromatics | 0.51 | 2.02 | 0.47 | 2.59 | 0.80 |
| Sum | 100.00 | 100.00 | 100.00 | 100.00 | 100.00 |
| C2/(C2-C4), % | 47.49 | 65.36 | 41.51 | 64.10 | 34.86 |

Under relatively mild process conditions of 450° C., $ZrO_2$-bound catalysts gave very high ethane yields and high ethane fractions out of $C_2$-$C_4$ yields. Catalyst Examples 5.1 and 5.3 gave 15% higher ethane yields and greater than 60% of ethane out of total $C_2$-$C_4$ combined on a weight basis in comparison with catalyst Example 1.2 as shown in Table 10. In contrast to $AlPO_4$-bound catalyst Example 1.2, dry oxidation after platinum incorporation consistently gave higher ethane yields and higher ethane fractions out of total $C_2$-$C_4$ product than the counterparts prepared using steam oxidation subsequent to the platinum incorporation step, whether employing chloroplatinic acid or tetraamine platinate as platinum precursors.

Example 16

Catalyst Examples 6.1 and 6.2 were tested following the protocol described in Example 9 using the feed composition in Table 11.

TABLE 11

| Component | nC5 | nC6 | iC6 | CH | MeCP | nC7 |
|---|---|---|---|---|---|---|
| wt % | 38.44 | 43.56 | 0.66 | 13.42 | 0.25 | 2.06 |

TABLE 12

| Catalyst Example | 6.1 | | | | 6.2 | | |
|---|---|---|---|---|---|---|---|
| Zeolite | MFI-40 | | | | MFI-500 | | |
| LN partial pressure, psia | 106 | 107 | 56 | 107 | 55 | 55 | 55 |
| H2 partial pressure, psia | 108 | 108 | 57 | 107 | 55 | 55 | 55 |
| WHSV, hr$^{-1}$ | 0.37 | 2.02 | 1.01 | 2.02 | 10.90 | 10.90 | 11.0 |
| Temperature, ° C. | 531 | 532 | 531 | 493 | 532 | 482 | 457 |
| Time, hours | 18.3 | 22.3 | 29.3 | 94.9 | 65.5 | 70.5 | 79.5 |
| C1 | 12.67 | 5.63 | 5.58 | 5.35 | 1.9 | 0.6 | 0.3 |
| C2 | 59.97 | 39.78 | 44.30 | 19.35 | 19.1 | 8.4 | 5.07 |
| C3 | 7.16 | 33.52 | 29.34 | 48.22 | 54.6 | 56.8 | 48.68 |
| C4 | 0.78 | 6.10 | 4.64 | 15.01 | 10.5 | 17.5 | 17.76 |
| Aromatics | 17.01 | 13.21 | 14.87 | 7.01 | 10.8 | 5.2 | 3.89 |
| Heavy Aromatics | 2.33 | 0.68 | 0.62 | 0.22 | 0.31 | 0.1 | 0.04 |
| Total Aromatics | 19.3 | 13.9 | 15.5 | 7.2 | 11.1 | 5.3 | 3.9 |
| Benzene | 4.57 | 2.12 | 2.85 | 0.84 | 2.54 | 1.83 | 2.17 |
| Toluene | 7.34 | 5.34 | 6.63 | 2.67 | 4.04 | 1.50 | 0.75 |
| Xylene | 3.55 | 3.82 | 4.08 | 2.55 | 3.02 | 1.26 | 0.59 |
| Ethylbenzene | 0.39 | 0.32 | 0.27 | 0.16 | 0.11 | 0.10 | 0.09 |
| A9 plus | 1.16 | 1.62 | 1.04 | 0.78 | 1.08 | 0.53 | 0.29 |
| C2-C4 | 67.91 | 79.41 | 78.29 | 82.57 | 84.1 | 82.7 | 71.5 |
| C2-C3 | 67.13 | 73.30 | 73.65 | 67.56 | 73.64 | 65.18 | 53.75 |
| C2/C3 | 8.38 | 1.19 | 1.51 | 0.40 | 0.35 | 0.15 | 0.10 |

As shown in Table 12 by operating at shorter contact times at higher WHSV using low activity zeolite with higher $Si/Al_2$ ratios such as in catalyst Example 6.2 as opposed to catalyst Example 6.1 operating at increased contact times at lower WHSV, the process can attain greater than 40% propane with predominant propane in $C_2$-$C_3$ aggregates or high $C_3/C_2$ (w/w) ratios from about 3 to about 10.

Example 17

Catalyst Example 7 comprising SAPO-11 was tested following the protocol described in Example 8 using the feed composition in Table 11.

TABLE 13

| Example | 17.1 | 17.2 | 17.3 | 17.4 |
|---|---|---|---|---|
| LN partial pressure, psia | 106 | 107 | 106 | 107 |
| H2 partial pressure, psia | 109 | 107 | 109 | 108 |
| WHSV, hr-1 | 1.95 | 10.90 | 1.95 | 5.41 |
| Temperature, ° C. | 455 | 454 | 530 | 530 |
| Time, hours | 3.5 | 17.6 | 42.6 | 47.6 |
| C1 | 1.6 | 0.2 | 4.0 | 1.3 |
| C2 | 4.4 | 0.8 | 14.1 | 7.7 |
| C3 | 32.5 | 9.6 | 47.2 | 42.4 |

TABLE 13-continued

| Example | 17.1 | 17.2 | 17.3 | 17.4 |
|---|---|---|---|---|
| C4 | 7.5 | 2.6 | 13.8 | 13.1 |
| Aromatics | 12.8 | 12.7 | 14.1 | 11.4 |
| Heavy Aromatics | 0.51 | 0.1 | 1.03 | 0.41 |
| Total Aromatics | 13.3 | 12.8 | 15.1 | 11.8 |
| Benzene | 11.86 | 12.34 | 8.77 | 7.83 |
| Toluene | 0.50 | 0.16 | 2.40 | 1.82 |
| Xylene | 0.12 | 0.02 | 1.09 | 0.83 |
| Ethylbenzene | 0.17 | 0.05 | 0.22 | 0.25 |
| A9 plus | 0.17 | 0.10 | 1.62 | 0.65 |
| C2-C4 | 44.4 | 13.0 | 75.1 | 63.2 |
| C2-C3 | 36.98 | 10.42 | 61.30 | 50.12 |
| C2/C3 | 0.14 | 0.08 | 0.30 | 0.18 |

Catalyst Example 7 made of SAPO-11 and exhibited consistently greater than 10% aromatics, out of which benzene is the primary aromatic over a broad range of temperatures and contact times. The high benzene yields are characteristic of facile conversions of cyclohexane to benzene as a result of elliptical pore shape of SAPO-11. Conceivably, for selectively converting naphthenic components to aromatics especially in high naphthene containing feeds, SAPO-11 can be deployed.

Example 18

Catalyst example 1.2 was evaluated to show its utility in converting full range naphtha (FRN) into effluents with $C_2$-$C_4$ streams of propane-rich, ethane-rich or comparable ethane and propane abundance. At temperatures between about 350 and about 460° C. and Hz/hydrocarbon molar ratios between about 2.5 and about 6.0, FRN was converted to an effluent containing greater than about 40% propane as shown in Table 14. At temperatures between about 450 and about 500° C. and Hz/hydrocarbon molar ratios between about 1.0 and about 3.0, FRN was converted to an effluent containing greater than about 40% ethane as shown Table 15.

TABLE 14

| | | | | | | | | | | | |
|---|---|---|---|---|---|---|---|---|---|---|---|
| Time, hours | | 37 | 42 | 50 | 56 | 60 | 70 | 77 | 90 | 96 | 108 |
| Bed Temperature, ° C. | | 349 | 375 | 375 | 375 | 401 | 401 | 426 | 451 | 451 | 451 |
| WHSV, hr$^{-1}$ | | 1.93 | 1.93 | 1.93 | 1.92 | 1.92 | 1.92 | 1.92 | 1.92 | 1.91 | 1.96 |
| H2/HCBN | | 2.83 | 2.84 | 4.25 | 5.67 | 5.67 | 2.84 | 4.25 | 5.69 | 4.26 | 2.78 |
| Reactor Inlet Pressure, psig | | 49.3 | 49.2 | 71.2 | 92.6 | 92.6 | 48.8 | 70.4 | 92.5 | 70.4 | 49.1 |
| | Feed | | | | | | | | | | |
| C1 | | 0.33 | 0.68 | 0.74 | 0.78 | 1.54 | 1.33 | 2.75 | 5.29 | 5.05 | 4.46 |
| C2s | | 3.44 | 5.95 | 5.78 | 5.72 | 9.37 | 9.88 | 14.66 | 21.32 | 22.25 | 26.26 |
| C3s | | 34.4 | 43.7 | 40.5 | 39.0 | 45.4 | 51.2 | 50.8 | 48.1 | 48.3 | 43.7 |
| C4s | | 23.2 | 20.1 | 22.3 | 23.2 | 19.4 | 13.3 | 10.0 | 5.9 | 4.6 | 3.8 |
| C5s | 0.06 | 7.67 | 4.17 | 5.58 | 6.47 | 3.03 | 1.55 | 0.62 | 0.17 | 0.14 | 0.18 |
| C6s | 10.82 | 3.09 | 0.89 | 1.12 | 1.29 | 0.26 | 0.21 | 0.08 | 0.05 | 0.06 | 0.07 |
| mCP + CH + MCH | 13.08 | 0.70 | 0.26 | 0.29 | 0.34 | 0.14 | 0.13 | 0.04 | 0.01 | 0.01 | 0.01 |
| C7-C9 NA | 59.9 | 13.1 | 10.1 | 10.0 | 10.1 | 7.3 | 8.5 | 7.4 | 6.3 | 6.4 | 7.5 |
| 1R Aromatics | 13.8 | 13.4 | 13.5 | 13.2 | 12.8 | 13.1 | 13.3 | 13.0 | 12.5 | 12.6 | 13.2 |
| Benzene | 0.32 | 0.90 | 0.93 | 0.89 | 0.82 | 0.98 | 1.10 | 1.19 | 1.45 | 1.58 | 1.98 |
| Toluene | 2.79 | 4.01 | 4.03 | 3.92 | 3.83 | 4.04 | 4.27 | 4.37 | 4.49 | 4.65 | 5.03 |
| Xylene | 6.14 | 5.74 | 5.84 | 5.71 | 5.67 | 5.59 | 5.56 | 5.15 | 4.55 | 4.43 | 4.15 |
| Ethylbenzene | 0.46 | 0.03 | 0.03 | 0.03 | 0.03 | 0.01 | 0.01 | 0.01 | 0.00 | 0.00 | 0.00 |
| A9 plus | 4.07 | 2.70 | 2.73 | 2.66 | 2.50 | 2.47 | 2.35 | 2.31 | 2.01 | 1.95 | 2.03 |
| Heavier | 2.33 | 0.63 | 0.65 | 0.52 | 0.38 | 0.45 | 0.63 | 0.68 | 0.41 | 0.48 | 0.83 |
| Sum | 100 | 100 | 100 | 100 | 100 | 100 | 100 | 100 | 100 | 100 | 100 |
| C2-C4 | | 61.1 | 69.7 | 68.5 | 67.8 | 74.2 | 74.4 | 75.5 | 75.3 | 75.2 | 73.7 |
| C2-C3 | | 37.9 | 49.6 | 46.3 | 44.7 | 54.8 | 61.1 | 65.4 | 69.4 | 70.6 | 69.9 |
| C2/C3 | | 0.10 | 0.14 | 0.14 | 0.15 | 0.21 | 0.19 | 0.29 | 0.44 | 0.46 | 0.60 |

TABLE 15

| | | | | | | | | | | |
|---|---|---|---|---|---|---|---|---|---|---|
| Time, hours | | 114 | 120 | 126 | 138 | 144 | 150 | 155 | 162 | 168 | 174 |
| Bed Temperature, ° C. | | 451 | 451 | 451 | 466 | 466 | 481 | 481 | 481 | 491 | 491 |
| WHSV, hr-1 | | 1.96 | 1.96 | 1.96 | 1.95 | 1.95 | 1.95 | 1.95 | 1.94 | 1.94 | 1.94 |
| H2/HCBN | | 2.79 | 2.08 | 1.38 | 2.09 | 2.80 | 2.79 | 2.07 | 1.39 | 1.41 | 2.11 |
| Reactor Inlet Pressure, psig | | 74.2 | 74.0 | 73.9 | 74.0 | 74.0 | 74.1 | 74.0 | 74.7 | 74.6 | 74.5 |
| | Feed | | | | | | | | | | |
| C1 | | 5.63 | 5.05 | 2.96 | 5.14 | 6.21 | 8.34 | 6.63 | 4.36 | 5.04 | 6.55 |
| C2s | | 28.1 | 41.8 | 44.4 | 40.5 | 31.0 | 44.2 | 53.7 | 48.8 | 50.9 | 46.4 |
| C3s | | 42.1 | 27.6 | 18.5 | 27.4 | 38.4 | 23.6 | 13.5 | 11.3 | 11.5 | 19.0 |
| C4s | | 3.5 | 3.4 | 2.9 | 3.3 | 3.3 | 2.2 | 1.6 | 1.5 | 1.5 | 2.2 |

TABLE 15-continued

| | | | | | | | | | | | |
|---|---|---|---|---|---|---|---|---|---|---|---|
| C5s | 0.06 | 0.16 | 0.29 | 0.32 | 0.27 | 0.16 | 0.11 | 0.12 | 0.13 | 0.13 | 0.15 |
| C6s | 10.82 | 0.06 | 0.08 | 0.09 | 0.09 | 0.06 | 0.05 | 0.06 | 0.07 | 0.06 | 0.07 |
| mCP + CH + MCH | 13.08 | 0.01 | 0.02 | 0.04 | 0.02 | 0.01 | 0.01 | 0.01 | 0.01 | 0.01 | 0.01 |
| C7-C9 NA | 59.9 | 6.9 | 6.3 | 6.7 | 7.0 | 6.9 | 6.6 | 6.4 | 6.9 | 6.0 | 6.6 |
| 1R Aromatics | 13.8 | 12.8 | 14.1 | 19.1 | 14.9 | 12.8 | 13.7 | 16.4 | 22.0 | 20.2 | 16.9 |
| Benzene | 0.32 | 2.04 | 2.63 | 3.75 | 2.76 | 2.12 | 2.90 | 3.82 | 4.47 | 4.68 | 3.45 |
| Toluene | 2.79 | 4.91 | 5.54 | 7.48 | 5.81 | 4.95 | 5.34 | 6.68 | 8.45 | 8.37 | 6.64 |
| Xylene | 6.14 | 3.95 | 3.96 | 5.10 | 4.17 | 3.85 | 3.43 | 3.92 | 5.72 | 4.89 | 4.37 |
| Ethylbenzene | 0.46 | 0.00 | 0.21 | 0.34 | 0.21 | 0.00 | 0.15 | 0.28 | 0.44 | 0.37 | 0.40 |
| A9 plus | 4.07 | 1.92 | 1.78 | 2.46 | 1.97 | 1.88 | 1.90 | 1.71 | 2.94 | 1.91 | 2.03 |
| Heavier | 2.33 | 0.71 | 1.40 | 4.88 | 1.41 | 1.14 | 1.25 | 1.61 | 4.96 | 4.65 | 2.10 |
| Sum | 100 | 100 | 100 | 100 | 100 | 100 | 100 | 100 | 100 | 100 | 100 |
| C2-C4 | | 73.7 | 72.7 | 65.8 | 71.2 | 72.7 | 69.9 | 68.7 | 61.6 | 63.9 | 67.6 |
| C2-C3 | | 70.2 | 69.4 | 62.9 | 67.8 | 69.4 | 67.8 | 67.1 | 60.1 | 62.4 | 65.5 |
| C2/C3 | | 0.67 | 1.52 | 2.40 | 1.48 | 0.81 | 1.88 | 3.99 | 4.32 | 4.42 | 2.44 |

Example 19

Catalyst Example 1.2 was evaluated to show its utility in converting a mixture of n-butane and iso-butane of equal weight percentages into effluents with $C_2$-$C_3$ streams of propane-rich, ethane-rich or comparable ethane and propane abundance. At temperatures between about 370 and about 470° C. and $H_2$/hydrocarbon molar ratios between about 1.0 and about 3.0, butanes were converted to an effluent containing greater than about 40% propane as shown Table 16. At temperatures between about 450 and about 500° C., more preferably between 460 and 490° C. and Hz/hydrocarbon molar ratios between about 1.0 and about 2.0, more preferably between about 1.0 and about 1.6, butanes were converted to an effluent containing greater than about 40% ethane as shown Table 17. At increased contact times at reduced WHSV, greater than 40% or more preferably greater than 50% ethane was produced at lower temperature ranges.

TABLE 16

| | | | | | | | | | | | | |
|---|---|---|---|---|---|---|---|---|---|---|---|---|
| Time, hours | 33 | 39 | 45 | 52 | 64 | 70 | 76 | 82 | 88 | 94 | 100 | 106 |
| Bed Temp., C | 374 | 375 | 400 | 401 | 426 | 426 | 426 | 451 | 452 | 451 | 467 | 467 |
| WHSV, hr$^{-1}$ | 1.96 | 1.96 | 1.96 | 1.96 | 1.96 | 1.96 | 1.95 | 1.95 | 1.96 | 1.96 | 1.96 | 1.96 |
| H2/C4s, molar | 1.53 | 1.02 | 1.02 | 1.52 | 2.04 | 1.54 | 1.02 | 1.02 | 1.53 | 2.03 | 2.03 | 1.53 |
| Reactor Inlet Pressure, psig | 75 | 75 | 75 | 76 | 76 | 75 | 75 | 75 | 75 | 76 | 76 | 75 |
| C1 | 0.8 | 0.8 | 2.5 | 1.9 | 4.1 | 4.1 | 3.4 | 5.8 | 6.9 | 7.2 | 9.9 | 9.3 |
| C2s | 3.2 | 3.9 | 10.3 | 7.9 | 14.2 | 15.8 | 19.1 | 41.3 | 27.4 | 23.4 | 31.6 | 40.3 |
| C3s | 25.7 | 39.1 | 55.6 | 45.8 | 54.8 | 61.3 | 64.8 | 41.0 | 57.6 | 59.5 | 52.9 | 43.7 |
| C4s | 62.5 | 49.0 | 27.9 | 39.9 | 24.9 | 17.3 | 11.1 | 6.3 | 6.8 | 9.0 | 4.7 | 4.5 |
| C5s | 6.43 | 6.12 | 2.86 | 4.24 | 1.92 | 1.28 | 0.91 | 0.63 | 0.38 | 0.41 | 0.19 | 0.28 |
| C6s | 0.40 | 0.40 | 0.09 | 0.14 | 0.06 | 0.05 | 0.09 | 0.10 | 0.05 | 0.03 | 0.03 | 0.04 |
| mCP + CH | 0.02 | 0.02 | 0.01 | 0.01 | 0.01 | 0.01 | 0.02 | 0.04 | 0.01 | 0.01 | 0.00 | 0.01 |
| C7-C9 NA | 0.59 | 0.33 | 0.41 | 0.04 | 0.02 | 0.04 | 0.17 | 0.19 | 0.28 | 0.19 | 0.14 | 0.21 |
| 1R Aromatics | 0.31 | 0.25 | 0.32 | 0.05 | 0.06 | 0.10 | 0.37 | 3.83 | 0.57 | 0.26 | 0.47 | 1.53 |
| Benzene | 0.03 | 0.02 | 0.02 | 0.01 | 0.01 | 0.02 | 0.05 | 0.55 | 0.08 | 0.05 | 0.10 | 0.25 |
| Toluene | 0.07 | 0.05 | 0.05 | 0.02 | 0.02 | 0.04 | 0.14 | 1.55 | 0.18 | 0.10 | 0.20 | 0.64 |
| Xylene | 0.10 | 0.06 | 0.07 | 0.02 | 0.02 | 0.03 | 0.12 | 1.25 | 0.13 | 0.06 | 0.11 | 0.42 |
| Ethylbenzene | 0.02 | 0.01 | 0.01 | 0.00 | 0.00 | 0.00 | 0.01 | 0.05 | 0.00 | 0.00 | 0.00 | 0.01 |
| A9 plus | 0.07 | 0.07 | 0.12 | 0.01 | 0.01 | 0.01 | 0.04 | 0.30 | 0.12 | 0.04 | 0.04 | 0.15 |
| Heavier | 0.03 | 0.05 | 0.05 | 0.00 | 0.00 | 0.00 | 0.04 | 0.93 | 0.08 | 0.02 | 0.02 | 0.19 |
| sum | 100.0 | 100.0 | 100.0 | 100.0 | 100.0 | 100.0 | 100.0 | 100.0 | 100.0 | 100.0 | 100.0 | 100.0 |
| C2-C3 | 28.9 | 43.0 | 65.9 | 53.7 | 69.0 | 77.1 | 83.9 | 82.4 | 85.0 | 82.9 | 84.5 | 84.0 |
| C2/C3 | 0.12 | 0.10 | 0.19 | 0.17 | 0.26 | 0.26 | 0.30 | 1.01 | 0.48 | 0.39 | 0.60 | 0.92 |

TABLE 17

| HOS | 100 | 106 | 112 | 141 | 185 | 210 | 234 | 239 |
|---|---|---|---|---|---|---|---|---|
| Bed Temp, °C. | 467 | 467 | 466 | 482 | 466 | 451 | 461 | 461 |
| WHSV, hr$^{-1}$ | 1.96 | 1.96 | 1.96 | 1.98 | 0.97 | 0.97 | 0.98 | 0.98 |
| H2/C4s, molar | 2.03 | 1.53 | 1.02 | 2.02 | 1.03 | 1.03 | 1.24 | 1.02 |
| Reactor Inlet Pressure, psig | 75.60 | 75.31 | 75.03 | 76.03 | 75.59 | 75.78 | 75.17 | 75.64 |
| C1 | 9.94 | 9.32 | 7.01 | 12.97 | 8.35 | 6.57 | 9.61 | 8.12 |
| C2s | 31.63 | 40.31 | 51.99 | 40.37 | 62.43 | 51.23 | 53.92 | 61.09 |
| C3s | 52.86 | 43.66 | 26.14 | 42.46 | 16.32 | 30.99 | 29.54 | 19.52 |
| C4s | 4.73 | 4.51 | 3.75 | 3.39 | 2.23 | 4.70 | 3.73 | 2.78 |
| C5s | 0.19 | 0.28 | 0.35 | 0.14 | 0.19 | 0.47 | 0.30 | 0.25 |
| C6s | 0.03 | 0.04 | 0.06 | 0.02 | 0.03 | 0.07 | 0.05 | 0.05 |
| mCP + CH | 0.00 | 0.01 | 0.02 | 0.01 | 0.01 | 0.04 | 0.03 | 0.01 |
| C7-C9 Non-Aromatics | 0.14 | 0.21 | 0.44 | 0.00 | 0.00 | 0.02 | 0.00 | 0.00 |
| 1R Aromatics | 0.47 | 1.53 | 7.85 | 0.62 | 7.48 | 4.83 | 2.47 | 6.16 |
| Benzene | 0.10 | 0.25 | 1.33 | 0.16 | 1.53 | 0.80 | 0.45 | 1.18 |
| Toluene | 0.20 | 0.64 | 3.17 | 0.29 | 3.14 | 2.00 | 1.06 | 2.58 |
| Xylene | 0.11 | 0.42 | 2.26 | 0.15 | 1.97 | 1.49 | 0.76 | 1.72 |
| Ethylbenzene | 0.00 | 0.01 | 0.14 | 0.00 | 0.12 | 0.07 | 0.02 | 0.09 |
| A9 plus | 0.04 | 0.15 | 0.65 | 0.02 | 0.51 | 0.35 | 0.15 | 0.43 |
| Heavier | 0.02 | 0.19 | 2.70 | 0.02 | 3.16 | 1.20 | 0.39 | 2.18 |
| Sum | 100.0 | 100.0 | 100.0 | 100.0 | 100.0 | 100.0 | 100.0 | 100.0 |
| C2-C3 | 84.5 | 84.0 | 78.1 | 82.8 | 78.8 | 82.2 | 83.5 | 80.6 |
| C2/C3 | 0.60 | 0.92 | 1.99 | 0.95 | 3.83 | 1.65 | 1.83 | 3.13 |

Example 20

Figure 5:
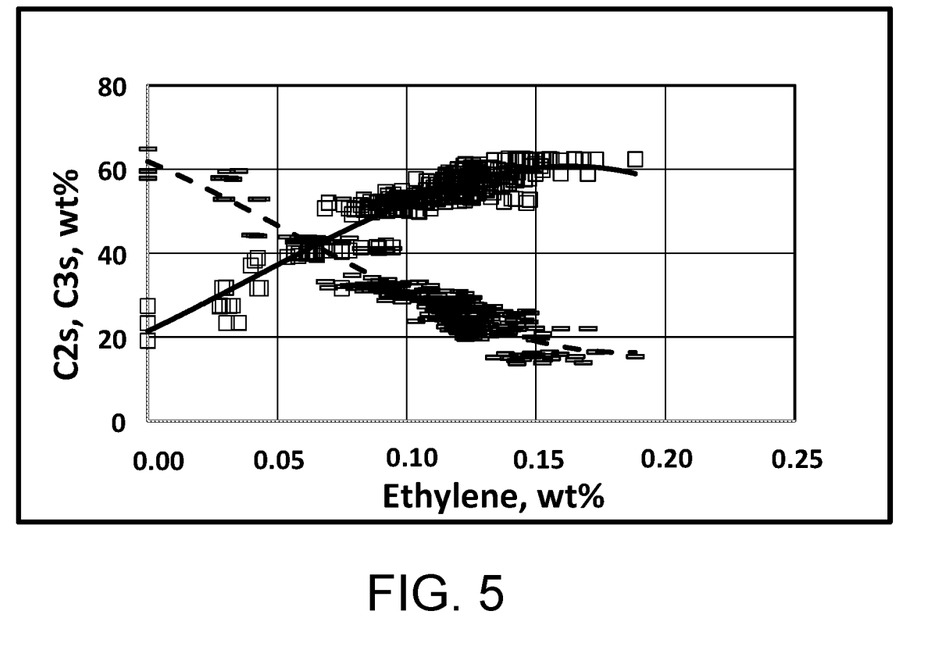
FIG. 5 is a plot of converting a 50/50 mixture of iso-butane and n-butane via olefinic intermediate.

We reacted a 50/50 mixture of isobutane and n-butane over a catalyst Example 1.2 according to the test procedure in Example 19 to produce ethane and propane. FIG. 5 depicts a plot of a 50/50 mixture of isobutane and n-butane reacting to produce ethane and propane as a function of an ethylene intermediate. The ethylene and ethane combined represented by squares increases in tandem with ethylene concentration, and plateaus out at around 60 wt % while propane represented by the flat rectangles decreases with increased ethylene concentration and levels out at around 20 wt % at an ethylene concentration of between about 0.15 and 0.20 wt %. The presence of ethylene evinces that interconversion to ethylene intermediate is taking place in the reaction of butanes to ethane and propane.

Specific Embodiments

While the following is described in conjunction with specific embodiments, it will be understood that this description is intended to illustrate and not limit the scope of the preceding description and the appended claims.

A first embodiment of the invention is a process for converting naphtha comprising contacting a naphtha stream with a zeolitic catalyst at conditions which dehydrogenate the paraffins to olefins, interconvert the olefins to lighter olefins and hydrogenate the lighter olefin to produce a light paraffin stream comprising ethane and propane. An embodiment of the invention is one, any or all of prior embodiments in this paragraph up through the first embodiment in this paragraph wherein a hydrogen to hydrocarbon ratio ranges from about 50% to about 500% of stoichiometric requirements to convert naphtha molecules to ethane and/or propane. An embodiment of the invention is one, any or all of prior embodiments in this paragraph up through the first embodiment in this paragraph wherein hydrogen to hydrocarbon molar ratio ranges from 0.3 to 15. An embodiment of the invention is one, any or all of prior embodiments in this paragraph up through the first embodiment in this paragraph wherein the pressure ranges from about 0.1 to about 3 MPa, space velocity ranges from about 0.3 to about 20 hr-1 and the temperatures ranges from about 350 to about 600° C. An embodiment of the invention is one, any or all of prior embodiments in this paragraph up through the first embodiment in this paragraph wherein a zeolite in the zeolitic catalyst comprises MFI, FER, MEL, UZM-39, UZM-44, UZM-54, MWW, MFS, AEL, MSE, UZM-35 and MTW. An embodiment of the invention is one, any or all of prior embodiments in this paragraph up through the first embodiment in this paragraph wherein the zeolite is an MFI having Si/Al2 molar ratios from about 20 to about 500. An embodiment of the invention is one, any or all of prior embodiments in this paragraph up through the first embodiment in this paragraph wherein the catalyst comprises a binder selected from alumina, silica, zirconia, titania and mixtures thereof. An embodiment of the invention is one, any or all of prior embodiments in this paragraph up through the first embodiment in this paragraph further comprising a phosphate in the binder. An embodiment of the invention is one, any or all of prior embodiments in this paragraph up through the first embodiment in this paragraph wherein more of the metal is on the binder than on the zeolite. An embodiment of the invention is one, any or all of prior embodiments in this paragraph up through the first embodiment in this paragraph further comprising steaming the catalyst. An embodiment of the invention is one, any or all of prior embodiments in this paragraph up through the first embodiment in this paragraph further comprising steaming the catalyst after the metal is added to the catalyst. An embodiment of the invention is one, any or all of prior embodiments in this paragraph up through the first embodiment in this paragraph wherein the metal comprises platinum, palladium, iridium, rhenium, ruthenium and mixtures of thereof. An embodiment of the invention is one, any or all of prior embodiments in this paragraph up through the first embodiment in this paragraph further comprising a modifier metal comprising tin, germanium, gallium, indium, thallium, zinc, silver and mixtures thereof. An embodiment of the invention is one, any or all of prior embodiments in this paragraph up through the first embodiment in this paragraph comprising about 0.01 to about 5 wt % metal on the catalyst. An embodiment of the invention is one, any or all of prior embodiments in this paragraph up through the first embodiment in this paragraph further comprising adding hydrogen to the naphtha stream. An embodiment of the invention is one, any or all of prior embodiments in this paragraph up through the first embodiment in this paragraph further comprising a molar ratio of hydrogen to hydrocarbon of about 0.5 to about 5 in the contacting step.

A second embodiment of the invention is a process for converting naphtha comprising contacting a naphtha stream with a zeolitic catalyst with more metal on the binder than on the zeolite at conditions which dehydrogenate paraffins to olefins, interconvert the olefins to lighter olefins and hydrogenate the lighter olefin to produce a light paraffin stream comprising ethane and propane. An embodiment of the invention is one, any or all of prior embodiments in this paragraph up through the second embodiment in this paragraph wherein the zeolite is an MFI having a Si/Al2 molar ratio from about 20 to about 500. An embodiment of the invention is one, any or all of prior embodiments in this paragraph up through the second embodiment in this paragraph further comprising steaming the catalyst after the metal is added to the catalyst.

A third embodiment of the invention is a process for converting naphtha to ethane and propane comprising contacting a naphtha stream with a catalyst comprising MFI zeolite with a Si/Al2 molar ratio of from about 20 to about 500 and/or an AEL molecular sieve and a metal on a binder at conditions which dehydrogenate paraffins to olefins and naphthene to aromatics, interconvert the olefins to lighter olefins and hydrogenate the lighter olefins to produce a light paraffin stream comprising ethane, propane and aromatics. Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for converting naphtha comprising:
    contacting a naphtha stream with a zeolitic catalyst at conditions which dehydrogenate paraffins to olefins, interconvert the olefins to lighter olefins and hydrogenate the lighter olefin to produce a light paraffin stream comprising ethane and propane.

2. The process of claim 1 wherein a hydrogen to hydrocarbon ratio ranges from about 50% to about 500% of stoichiometric requirements to convert naphtha molecules to ethane and/or propane.

3. The process of claim 1 wherein hydrogen to hydrocarbon molar ratio ranges from 0.3 to 15.

4. The process of claim 1 wherein the pressure ranges from about 0.1 to about 3 MPa, space velocity ranges from about 0.3 to about 20 hr$^{-1}$ and the temperatures ranges from about 350 to about 600° C.

5. The process of claim 1 wherein a zeolite in said zeolitic catalyst comprises MFI, FER, MEL, UZM-39, UZM-44, UZM-54, MWW, MFS, AEL, MSE, UZM-35 and MTW.

6. The process of claim 5 wherein the zeolite is an MFI having Si/Al$_2$ molar ratios from about 20 to about 500.

7. The process of claim 1 wherein the catalyst comprises a binder selected from alumina, silica, zirconia, titania and mixtures thereof.

8. The process of claim 7 further comprising a phosphate in the binder.

9. The process of claim 1 further comprising a metal on the catalyst.

10. The process of claim 7 wherein more of the metal is on the binder than on the zeolite.

11. The process of claim 9 further comprising steaming the catalyst.

12. The process of claim 9 further comprising steaming the catalyst after the metal is added to the catalyst.

13. The process of claim 9 wherein the metal comprises platinum, palladium, iridium, rhenium, ruthenium and mixtures of thereof.

14. The process of claim 9 further comprising a modifier metal comprising tin, germanium, gallium, indium, thallium, zinc, silver and mixtures thereof.

15. The process of claim 9 comprising about 0.01 to about 5 wt % metal on the catalyst.

16. The process of claim 1 further comprising adding hydrogen to the naphtha stream.

17. The process of claim 1 further comprising a molar ratio of hydrogen to hydrocarbon of about 0.5 to about 5 in the contacting step.

18. A process for converting naphtha comprising contacting a naphtha stream with a zeolitic catalyst with more metal on the binder than on the zeolite at conditions which dehydrogenate paraffins to olefins, interconvert the olefins to lighter olefins and hydrogenate the lighter olefin to produce a light paraffin stream comprising ethane and propane.

19. The process of claim 17 wherein the zeolite is an MFI having a Si/Al$_2$ molar ratio from about 20 to about 500.

20. The process of claim 18 further comprising steaming the catalyst after the metal is added to the catalyst.

21. A process for converting naphtha to ethane and propane comprising: contacting a naphtha stream with a catalyst comprising MFI zeolite with a Si/Al$_2$ molar ratio of from about 20 to about 500 and/or an AEL molecular sieve and a metal on a binder at conditions which dehydrogenate the paraffins to olefins and naphthene to aromatics, interconvert the olefins to lighter olefins and hydrogenate the lighter olefins to produce a light paraffin stream comprising ethane, propane and aromatics.

* * * * *